US008716333B2

(12) United States Patent
Hudlicky et al.

(10) Patent No.: US 8,716,333 B2
(45) Date of Patent: May 6, 2014

(54) PROCESS AND COMPOUNDS FOR THE MANUFACTURE OF OSELTAMIVIR AND ANALOGS THEREOF, AND NEW ANTIVIRAL AGENTS

(75) Inventors: Tomas Hudlicky, St. Catharines (CA); Lukas Werner, Kadan (CS); Ales Machara, Brevnov (CS)

(73) Assignee: Brock University, St. Catharines, ON (CA)

( * ) Notice: Subject to any disclaimer, the term of this patent is extended or adjusted under 35 U.S.C. 154(b) by 0 days.

(21) Appl. No.: 13/502,375

(22) PCT Filed: Oct. 15, 2010

(86) PCT No.: PCT/CA2010/001639
§ 371 (c)(1), (2), (4) Date: Jun. 21, 2012

(87) PCT Pub. No.: WO2011/047466
PCT Pub. Date: Apr. 28, 2011

(65) Prior Publication Data

US 2012/0252890 A1 Oct. 4, 2012

Related U.S. Application Data

(60) Provisional application No. 61/254,311, filed on Oct. 23, 2009.

(51) Int. Cl.

| | |
|---|---|
| ***A61K 31/357*** | (2006.01) |
| ***C07D 317/46*** | (2006.01) |
| ***C07D 203/26*** | (2006.01) |
| ***C07C 229/48*** | (2006.01) |

(52) U.S. Cl.
USPC ............ 514/465; 548/961; 549/436; 560/125

(58) Field of Classification Search
USPC ............ 514/465; 548/961; 560/125; 549/436
See application file for complete search history.

(56) References Cited

FOREIGN PATENT DOCUMENTS

WO WO2009137916 11/2009

OTHER PUBLICATIONS

Scaffidi et al., The synthesis and biological evaluation of some carbocyclic analogues of PUGNAc, 2008, Carbohydrate Research, 343, 2744-2753.*

Werner, Lukas et al., "Synthesis of 1,2- and 1,4-amino alcohols from 1,3-dienes via oxazines. Rearrangments of 1,4-amino alcohol derivatives to oxazolines", Tetrahedron, 2010, vol. 66, pp. 3671-3769.

Scaffidi, Adrian, et al., "The synthesis and biological evaluation of some carbocyclic analogues of PUGNAc", Carbohydrate Research, vol. 343, 2008, pp. 2744-2753.

Werner, Lukas, et al., "Short Chemoenzymatic Azide-Free Synthesis of Oseltamivir (Tamiflu): Approaching the Potential for Process Efficiency", Adv. Synth. Catal., 2010, vol. 352, pp. 195-200.

Fabris, Fabrizio, et al., "Investigation of steric and functionality limits in the enzymatic dihydroxylation of benzoate esters. Versatile intermediates for the synthesis of pseudo-sugars, amino cyclitols, and bicyclic ring systems", Organic & Biomolecular Chemistry, 2009, vol. 7, pp. 2619-2627.

Sullivan, Bradford, et al., "Symmetry-Based Design for the Chemoenzymatic Synthesis of Oseltamivir (Tamiflu) from Ethyl Benzoate", Angew. Chem. Int. Ed., 2009, vol. 48, pp. 4229-4231.

International Search Report and Written Opinion of PCT/CA2010/001639 completed on Jan. 21, 2011.

Kim, Choung U., et al., "Structure-Activity Relationship Studies of Novel Carbocyclic Influenza Neuraminidase Inhibitors", J. Med. Chem, 1998, vol. 41, pp. 2451-2460.

* cited by examiner

*Primary Examiner* — Kristin Vajda
(74) *Attorney, Agent, or Firm* — Richard S. Echler; Patricia L. Folkins

(57) ABSTRACT

The present application relates to processes for the preparation of intermediates useful in the manufacture of oseltamivir and the $H_3PO_4$ salt of oseltamivir, Tamiflu®. The application further relates to novel intermediate and compounds and oseltamivir analogs and to pharmaceutical compositions comprising said analog compounds. The application further relates to a method of using the novel analogs of oseltamivir to treat or prevent influenza.

35 Claims, No Drawings

PROCESS AND COMPOUNDS FOR THE MANUFACTURE OF OSELTAMIVIR AND ANALOGS THEREOF, AND NEW ANTIVIRAL AGENTS

This application is a National Stage of co-pending International Application No. PCT/CA2010/001639 filed Oct. 15, 2010, which claims the benefit of Provisional Application No. 61/254,311, filed Oct. 23, 2009, the contents of both of which are herein incorporated in their entirety by reference.

FIELD OF THE APPLICATION

The present application relates to novel intermediates and processes for the preparation of oseltamivir, and oseltamivir phosphate (Tamiflu®) from readily available precursors and to uses of these certain intermediates and analogs as medicaments.

BACKGROUND OF THE APPLICATION

The possibility of a major influenza pandemic (especially the avian H1N1 influenza) continues to be a serious health concern. The development of effective antiviral medicines is hampered by the exceptionally high mutation rates of influenza virus. Therefore, in order to be successful, new drugs should target the molecular mechanisms specific to the proliferation of the virus. The mechanism of infection involves the protein neuraminidase (NA), essential to viral replication. NA is responsible for the glycosidic cleavage of sialic acid (A) (in Scheme 1) from a glycoprotein of a host cell in a process that liberates the virion from the infected cell [(a) Russell, R. J.; Haire, L. F.; Stevens, D. J.; Collins, P. J.; Lin, Y. P.; Blackburn, G. M.; Hay, A. J.; Gamblin, S. J.; Skehel, J. J. *Nature* 2006, 443, 45; (b) Colman, P. M.; Varghese, J. N.; Layer, W. G. *Nature* 1983, 303, 41]. The NA protein active site appears to be conserved in many strains of the influenza A and B virus. Therefore, an efficient inhibitor of the NA protein could provide a broad-spectrum anti-influenza drug. Two compounds have been found most effective in mimicking the oxonium intermediate of sialic acid glycolysis, (i.e. structure (B) in Scheme 1), and hence acting as excellent inhibitors of NA: zanamivir (C) and oseltamivir phosphate (1a), Tamiflu® (also shown in Scheme 1). Tamiflu® appears to be superior to zanamivir because it is orally active and serves as prodrug, the active form of which is the corresponding carboxylic acid. It also has a superior bioavailability and is active at nanomolar levels. For the most recent reviews of Tamiflu® activity, supply problems, and its syntheses see: Shibasaki, M.; Kanai, M. *Eur. J. Org. Chem.* 2008, ASAP web edition; (b) Farina, V.; Brown, J. D. *Angew. Chem. Int. Ed.* 2006, 45, 7330.

Oseltamivir is not a complex molecule yet its practical synthesis on a scale large enough to guard against an influenza pandemic presents a formidable challenge. Stockpiles of Tamiflu® and similar agents are currently the focus of many governments worldwide.

Scheme 1

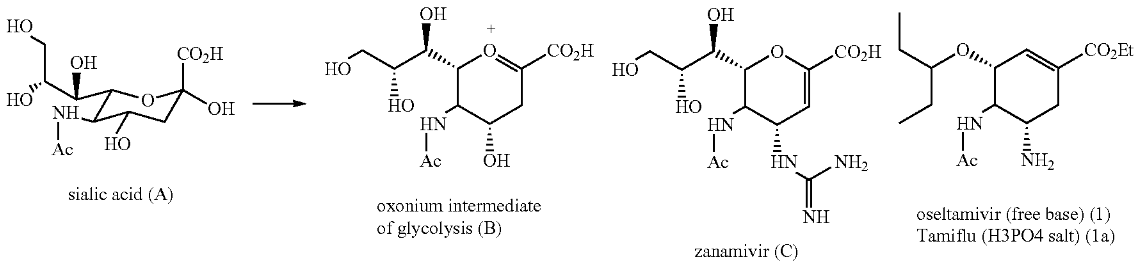

sialic acid (A)

oxonium intermediate of glycolysis (B)

zanamivir (C)

oseltamivir (free base) (1)
Tamiflu (H3PO4 salt) (1a)

A formal chemoenzymatic synthesis of oseltamivir (1) from ethyl benzoate in ten steps compressed to just seven operations was recently reported (Sullivan, B.; Carrera, I.; Drouin, M.; Hudlicky, T. *Angew. Chem. Int. Ed.* 2009, 48, 4229-4231). While this particular synthesis compared very favorably with most preparations reported to date it still relied on the use of azide as means of introduction of the C-5 amino group [for the most recent reviews of approaches to oseltamivir or Tamiflu® see: (a) J. Magano *Chem. Rev.* 2009, 109, 4398; (b) Shibasaki, M.; Kanai, M. *Eur. J. Org. Chem.* 2008, 11, 1839; (c) Farina, V.; Brown, J. D. *Angew. Chem. Int. Ed.* 2006, 45, 7330, Hudlicky, T. PCT Patent Application No. PCT/CA20009/000622, May 12, 2009]. For other syntheses of oseltamivir or Tamiflu® previously reported in the literature see: (a) Kim, C. U.; Lew, W.; Williams, M. A.; Liu, H.; Zhang, L.; Swaminathan, S.; Bischofberger, N.; Chen, M. S.; Mendel, D. B.; Tai, C. Y.; Layer, W. G.; Stevens, R. C. *J. Am. Chem. Soc.* 1997, 119, 681; (b) Kim, C. U.; Lew, W.; Williams, M. A.; Wu, H.; Zhang, L.; N.; Chen, X.; Escarpe, P. A.; Mendel, D. B.; Layer, W. G.; Stevens, R. C. *J. Med. Chem.* 1998, 41, 2451; (c) Rohloff, J. C.; Kent, K. M.; Postich, M. J.; Becker, M. W.; Chapman, H. H.; Kelly, D. E.; Lew, W.; Louie, M. S.; McGee, L. R.; Prisbe, E. J.; Schultze, L. M.; Yu, R. H.; Zhang, L. *J. Org. Chem.* 1998, 63, 4545; (d) M. Federspiel, R. Fischer, M. Hennig, H.-J. Mair, T. Oberhauser, G. Rimmler, T. Albiez, J. Bruhin, H. Estermann, C. Gandert, V. Göckel, S. Götzö, U. Hoffmann, G. Huber, G. Janatsch, S. Lauper, O. Röckel-Stäbler, R. Trussardi, A. G. Zwahlen *Org. Process Res. Dev.* 1999, 3, 266; (e) Karpf, M.; Trussardi, R. *J. Org. Chem.*, 2001, 66, 2044; (f) Harrington, P. J.; Brown, J. D.; Foderaro, T.; Hughes, R. C. *Org. Proc. Res. Dev.*, 2004, 8, 86; (g) Sungwoo Hong, Y.; Corey, E. J. *J. Am. Chem. Soc.* 2006, 128, 6310; (h) Fukuta, Y.; Mita, T.; Fukuda, N.; Kanai, M.; Shibasaki, M. *J. Am. Chem. Soc.* 2006, 128, 6312.; (i) Cong, X.; Yao, J.-Z. *J. Org. Chem.* 2006, 71, 5365; (j) Shie, J.-J.; Fang, J.-M.; Wang, S.-Y.; Tsai, K.-C.; Cheng, Y.-S. E.; Yang, A.-S.; Hsiao, S.-C.; Su, C.-Y.; Wong, C.-H. *J. Am. Chem. Soc.* 2007, 129, 11892; (k) Satoh, N.; Akiba, T.; Yokoshima, S.; Fukuyama, T. *Angew. Chem. Int. Ed.* 2007, 46, 5734; (l) Bromfield, K. M.; Gradén, H.; Hagberg, D. P.; Olsson, T.; Kann, N. *Chem. Commun.* 2007, 3183; (m) Mita, T.; Fukuda, N.; Roca, F. X.; Kanai, M.; Shibasaki, M. *Org. Lett.* 2007, 9, 259; (n) Yamatsugu, K.; Kamijo, S.; Suto, Y.; Kanai, M.; Shibasaki, M. *Tetrahedron Lett.* 2007, 48, 1403; (o)

Matveenko, M.; Willis, A. C.; Banwell, M. G. *Tetrahedron Lett.* 2008, 49, 7018; (p) Shie, J.-J.; Fang, J.-M.; Wong, C.-H. *Angew. Chem. Int. Ed.* 2008, 47, 5788; (q) Kipassa, N. T.; Okamura, H.; Kina, K.; Hamada, T.; Iwagawa, T. *Org. Lett.* 2008, 10, 815; (r) Trost, B. M.; Zhang, T. *Angew. Chem. Int. Ed.* 2008, 120, 3819; (s) Zutter, U.; Iding, H.; Spurr, P.; Wirz, B. *J. Org. Chem.* 2008, 73, 4895; (t) Ishikawa, H.; Suzuki, T.; Hayashi, Y. *Angew. Chem. Int. Ed.* 2009, 48, 1304; (u) Yamatsugu, K.; Yin, L.; Kamijo, S.; Kimura, Y.; Kanai, M.; Shibasaki, M. *Angew. Chem. Int. Ed.* 2009, 48, 1070; (v) Oshitari, T.; Mandai, T. *Synlett* 2009, 787; (w) Carbain, B.; Martin, S. R; Collins, P. J.; Hitchcock, P. B.; Streicher, H. *Org. Biomol. Chem.*, 2009, 7, 257; (x) Yamatsugu, K.; Kanai, M; Shibasaki, M. *Tetrahedron* 2009, 65, 601; (y) Resende, R.; Glover C.; Watts, A. G. *Tetrahedron Lett.* 2009, 50, 4009. For previously reported commercial syntheses see: (a) Kim, C. U.; Lew, W.; Williams, M. A.; Liu, H.; Zhang, S.; Swaminathan, S.; Bischofberger, N.; Chen, M. S.; Mendel, D. B.; Tai, C. Y.; Layer, W. G.; Stevens, R. C. *J. Am. Chem. Soc.* 1997, 119, 681; (b) Rohloff, J. C.; Kent, K. M.; Postich, M. J.; Becker, M. W.; Chapman, H. H.; Kelly, D. E.; Lew, W.; Louie, M. S.; McGee, L. R.; Prisbe, E. J.; Schultze, L. M.; Yu, R. H.; Zhang, L. *J. Org. Chem.* 1998, 63, 4545; (c) M. Federspiel, R. Fischer, M. Hennig, H.-J. Mair, T. Oberhauser, G. Rimmler, T. Albiez, J. Bruhin, H. Estermann, C. Gandert, V. Göckel, S. Götzö, U. Hoffmann, G. Huber, G. Janatsch, S. Lauper, O. Röckel-Stäbler, R. Trussardi, A. G. Zwahlen *Org. Process Res. Dev.* 1999, 3, 266; (d) Abrecht, S.; Federspiel, M. C.; Estermann, H.; Fischer, R.; Karpf, M.; Mair, H.-J.; Oberhauser, T.; Rimmler, G.; Trussardi, R.; Zutter, U. *Chimia* 2007, 61, 93].

SUMMARY OF THE APPLICATION

The preparation of novel intermediates that are useful in the preparation of oseltamivir and analogs thereof is reported herein. Using starting materials previously reported in the art, the process of the present application allows the incorporation of the C-5 amino functionality of oseltamivir without the use of an azide reagent, a significant advantage over previously reported processes. The present process also includes one of the shortest overall routes to oseltamivir. In one embodiment, the intermediate prepared using the process of the present application is obtained from readily available cis-diol alkyl benzoates in just seven chemical steps that can be carried out in five transformations, the entire sequence not requiring chromatography. The intermediate obtained using the process of the present application has been previously converted to oseltamivir using 3 or 4 synthetic steps.

Accordingly, the present application includes a process for the preparation of a compound of formula I:

I

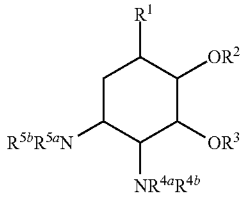

wherein $R^1$ is $CO_2Et$ or a functional group that can be converted to $CO_2Et$;

$R^2$ and $R^3$ are independently, suitable protecting groups, or $R^2$ and $R^3$ are joined to form a suitable protecting group;

$R^{4a}$ and $R^{4b}$ are independently selected from H and a suitable protecting group or $R^{4a}$ and $R^{4b}$ are joined to form a suitable protecting group;

$R^{5a}$ and $R^{5b}$ are independently selected from H and a suitable protecting group or $R^{5a}$ and $R^{5b}$ are joined to form a suitable protecting group;

the process comprising:

(i) treating a compound of the formula II, wherein $R^1$, $R^2$, $R^3$, $R^{4a}$ and $R^{4b}$ are as defined in formula I under conditions for the [3,3] oxidative rearrangement of the allylic alcohol to provide a compound of the formula III, wherein $R^1$, $R^2$, $R^3$, $R^{4a}$ and $R^{4b}$ are as defined in formula I,

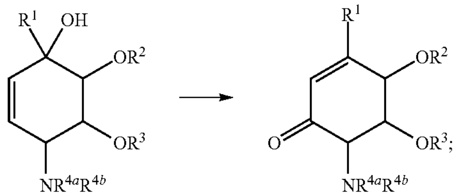

II III (ii) converting the compound of the formula III, wherein $R^1$, $R^2$, $R^3$, $R^{4a}$ and $R^{4b}$ are as defined in formula I, to a compound of the formula IV, wherein $R^1$, $R^2$, $R^3$, $R^{4a}$ and $R^{4b}$ are as defined in formula I and $R^7$ is a group that is removed under reduction or hydrogenation reaction conditions or $R^7$ is a suitable acid labile protecting group,

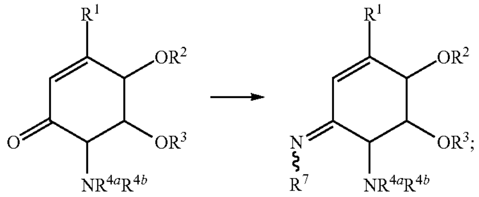

III IV and (iii) reducing or hydrogenating the compound of the formula IV, optionally in the presence of a suitable protecting group reagent, to provide compounds of the formula I, wherein:

(a) $R^{5a}$ and $R^{5b}$ are H when $R^7$ is a group that is removed under reduction or hydrogenation reaction conditions and the suitable protecting group reagent is not present;

(b) one of $R^{5a}$ and $R^{5b}$ is H and the other is a suitable protecting group or $R^{5a}$ and $R^{5b}$ are joined to form a suitable protecting group when $R^7$ is a group that is removed under reduction or hydrogenation reaction conditions and the suitable protecting group reagent is present; or (c) one of $R^{5a}$ and $R^{5b}$ is H and the other is a suitable acid labile protecting group when $R^7$ is a suitable acid labile protecting group,

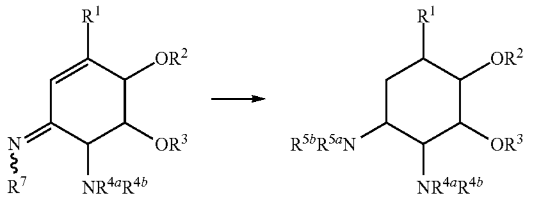

IV I wherein, in the compounds of the formulae I, II, III and/or IV, one or more available hydrogens in $R^1$, $R^2$, $R^3$, $R^{4a}$, $R^{4b}$, $R^{5a}$, $R^{5b}$ and/or $R^7$ is/are optionally replaced with F and/or one or more of available atoms in the compounds of the formulae I, II, III and/or IV is/are optionally replaced with an isotopic label.

Also within the scope of the present application are novel intermediate compounds for the preparation of oseltamivir and analogs thereof. Accordingly, the application includes a compound of formula III:

III

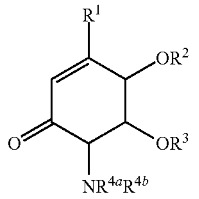

wherein $R^1$ is $CO_2Et$ or a functional group that can be converted to $CO_2Et$;

$R^2$ and $R^3$ are independently selected from H and a suitable protecting group, or $R^2$ and $R^3$ are joined to form a suitable protecting group; and $R^{4a}$ and $R^{4b}$ are independently selected from H and a suitable protecting group or $R^{4a}$ and $R^{4b}$ are joined to form a suitable protecting group;

wherein, one or more available hydrogens in $R^1$, $R^2$, $R^3$, $R^{4a}$ and/or $R^{4b}$ is/are optionally replaced with F and/or one or more of available atoms is/are optionally replaced with an isotopic label, or a salt and/or solvate thereof.

The application also includes a compounds of formula IV:

IV

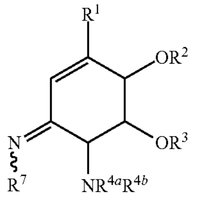

wherein $R^1$ is $CO_2Et$ or a functional group that can be converted to $CO_2Et$;

$R^2$ and $R^3$ are independently selected from H and a suitable protecting group, or $R^2$ and $R^3$ are joined to form a suitable protecting group;

$R^{4a}$ and $R^{4b}$ are independently selected from H and a suitable protecting group or $R^{4a}$ and $R^{4b}$ are joined to form a suitable protecting group; and $R^7$ is a group that is removed under reduction or hydrogenation reaction conditions or $R^7$ is a suitable acid labile protecting group, wherein, one or more available hydrogens in $R^1$, $R^2$, $R^3$, $R^{4a}$, $R^{4b}$ and/or $R^7$ is/are optionally replaced with F and/or one or more of available atoms is/are optionally replaced with an isotopic label, or a salt, solvate and/or prodrug thereof.

Certain compounds disclosed herein have been shown to have antiviral activity. Accordingly, the present application also includes a compound of formula V:

V

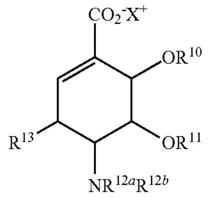

wherein $R^{10}$ and $R^{11}$ are independently selected from H, $C_{1-6}$alkyl and $C_{1-6}$acyl, or $R^{10}$ and $R^{11}$ are joined, together with the atoms to which they are attached, to form a 5-10-membered ring that is unsubstituted or substituted with one or more of halo or $C_{1-6}$alkyl;

$R^{12a}$ and $R^{12b}$ are independently selected from H, $C_{1-6}$alkyl and $C_{1-6}$acyl;

$R^{13}$ is selected from $OR^{14}$ and $NR^{15a}R^{15b}$ or $R^{13}$ is $=O$ or $=NR^{16}$;

$R^{14}$ is selected from H, $C_{1-6}$alkyl and $C_{1-6}$acyl;

$R^{15a}$ and $R^{15b}$ are independently selected from H, $C_{1-6}$alkyl and $C_{1-6}$acyl;

$R^{16}$ is selected from H, OH, $C_{1-6}$alkyl, $OC_{1-6}$alkyl, $C_{1-6}$acyl, $OC_{1-6}$acyl, $NH_2$, $NHC_{1-6}$alkyl, $N(C_{1-6}alkyl)(C_{1-6}alkyl)$ and $NHC_{1-6}$acyl, or $R^{16}$ and one of $R^{12a}$ and $R^{12b}$ form a linker group "-A-C(O)-" to provide a compound of the formula:

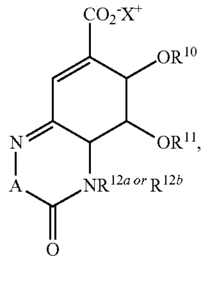

wherein A is O or NH;

$X^+$ is a cation; and one or more available hydrogens in $R^{10}$, $R^{11}$, $R^{12a}$, $R^{12b}$, $R^{13}$, $R^{14}$, $R^{15a}$, $R^{15b}$ and/or $R^{16}$ is/are optionally replaced with F and/or one or more of available atoms in the compounds of the formula is/are optionally replaced with an isotopic label, or a pharmaceutically acceptable salt and/or solvate thereof.

In a specific embodiment of the present application there is also included a compound of formula V:

V

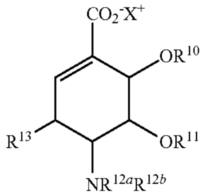

wherein $R^{10}$ and $R^{11}$ are independently selected from H, $C_{1-6}$alkyl and $C_{1-6}$acyl, or $R^{10}$ and $R^{11}$ are joined, together with the atoms to which they are attached, to form a 5-10-membered ring that is unsubstituted or substituted with one or more of halo or $C_{1-6}$alkyl;

$R^{12a}$ and $R^{12b}$ are independently selected from H, $C_{1-6}$alkyl and $C_{1-6}$acyl;

$R^{13}$ is $=NR^{16}$;

$R^{16}$ is selected from H, OH, $C_{1-6}$alkyl, $OC_{1-6}$alkyl, $C_{1-6}$acyl, $OC_{1-6}$acyl, $NH_2$, $NHC_{1-6}$alkyl, $N(C_{1-6}alkyl)(C_{1-6}alkyl)$ and $NHC_{1-6}$acyl, or $R^{16}$ and one of $R^{12a}$ and $R^{12b}$ form a linker group "-A-C(O)-" to provide a compound of the formula:

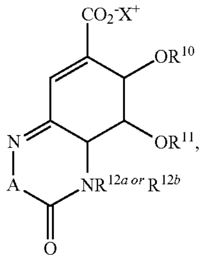

wherein A is O or NH;

$X^+$ is a cation; and one or more available hydrogens in $R^{10}$, $R^{11}$, $R^{12a}$, $R^{12b}$, $R^{13}$, $R^{14}$, $R^{15a}$, $R^{15b}$ and/or $R^{16}$ is/are optionally replaced with F and/or one or more of available atoms in the compounds of the formula is/are optionally replaced with an isotopic label, or a pharmaceutically acceptable salt, solvate and/or prodrug thereof.

The present application also includes a compound of the formula VI:

VI

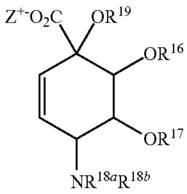

wherein $R^{16}$ and $R^{17}$ are independently selected from H, $C_{1-6}$alkyl and $C_{1-6}$acyl, or $R^{16}$ and $R^{17}$ are joined together to form, together with the atoms to which they are attached, a 5-10-membered ring that is unsubstituted or substituted with one or more of halo or $C_{1-4}$alkyl;

$R^{18a}$ and $R^{18b}$ are independently selected from H, $C_{1-6}$alkyl and $C_{1-6}$acyl;

$R^{19}$ is selected from H, $C_{1-6}$alkyl and $C_{1-6}$acyl;

$Z^+$ is a cation; and one or more available hydrogens in $R^{16}$, $R^{17}$, $R^{18a}$, $R^{18b}$ and/or $R^{19}$ is/are optionally replaced with F and/or one or more of available atoms in the compounds of the formula is/are optionally replaced with an isotopic label, or a pharmaceutically acceptable salt and/or solvate thereof.

The present application also includes the use of one or more compounds of the formula V or VI, or a pharmaceutically acceptable salt, solvate, prodrug and/or stereoisomer thereof, as a medicament.

Another aspect of the application includes a use of one or more compounds of the formula V or VI, or a pharmaceutically acceptable salt, solvate, prodrug and/or stereoisomer thereof, for the treatment or prevention of influenza.

Another aspect of the application includes a use of one or more compounds of the formula V or VI, or a pharmaceutically acceptable salt, solvate, prodrug and/or stereoisomer thereof, for the preparation of a medicament for the treatment or prevention of influenza.

Another aspect of the application includes one or more compounds of the formula V or VI, or a pharmaceutically acceptable salt, solvate, prodrug and/or stereoisomer thereof, for use to treat or prevent of influenza.

Also within the scope of the present application is a method of treating or preventing influenza comprising administering an effective amount of one or more compounds of the formula V or VI, or a pharmaceutically acceptable salt, solvate, prodrug and/or stereoisomer thereof to a subject in need thereof.

The one or more compounds of the formula V or VI, or a pharmaceutically acceptable salt, solvate, prodrug and/or stereoisomer thereof, are suitably formulated into pharmaceutical compositions for administration to human subjects in a biologically compatible form suitable for administration in vivo. Accordingly, the present application further includes a pharmaceutical composition comprising one or more compounds of the formula V or VI, or a pharmaceutically acceptable salt, solvate, prodrug and/or stereoisomer thereof, and a pharmaceutically acceptable carrier and/or diluent.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

DETAILED DESCRIPTION OF THE APPLICATION

(I) Definitions

The definitions and embodiments described in this section are intended to be applicable to all embodiments herein described for which they are suitable as would be understood by a person skilled in the art.

The term "alkyl" as used herein, whether it is used alone or as part of another group, means straight or branched chain, saturated alkyl groups. Generally a "lower alkyl group" contains 1, 2, 3, 4, 5, or 6 atoms (i.e. $C_{1-6}$alkyl) and the like, and a "higher alkyl group" contains greater than 6 and up to 20 carbon atoms. It is an embodiment of the application that the alkyl groups are optionally substituted. It is a further embodiment that, in the alkyl groups, one or more, including all, of the hydrogen atoms are optionally replaced with F or $^2H$ and thus includes, for example trifluoromethyl, pentafluoroethyl and the like.

The term "aryl" as used herein refers to cyclic groups that contain at least one aromatic ring. The cyclic groups are either monocyclic, bicyclic or tricyclic, and, when more than one ring is present, the rings are joined in fused, spiro and/or bridged arrangements. In an embodiment of the application, the aryl group contains from 6 to 14 atoms. In a further embodiment, one or more of the atoms in the aryl group is optionally substituted (i.e. is bonded to a group other than H). It is an embodiment that the aryl group is a phenyl group that is optionally substituted with one to five F atoms.

The term "heteroaryl" as used herein refers to cyclic groups that contain at least one heteroaromatic ring. The cyclic groups are either monocyclic, bicyclic or tricyclic, and, when more than one ring is present, the rings are joined in fused, spiro and/or bridged arrangements. In an embodiment of the application, the aryl group contains from 5 to 14 atoms, of which one or more atoms is a heteroatom, for example, O, S, N, P or Si. In a further embodiment, one or more of the atoms in the aryl group is optionally substituted (i.e. is bonded to a group other than H). It is an embodiment that the aryl group is a phenyl group that is optionally substituted with one to five F atoms.

The term "halo" as used herein refers to a halogen atom and includes F, Cl, Br and I.

The term "optionally substituted with one or more $C_{1-6}$alkyl" as used herein means that the referenced group is either unsubstituted or substituted with one or more, suitably one or two, $C_{1-6}$alkyl groups.

The symbol "∿∿" indicates that that the stereochemistry of the bond is variable. For example, when attached to a double bond, this bond symbol indicates that the group bonded to the double bond is in either the cis or trans configuration or the compound comprises a mixture of both configurations.

The term "optionally substituted" as used herein means that the referenced group is unsubstituted or substituted with one or more groups that are compatible with the reaction conditions utilized herein and do not impede, but may actually promote, the reaction processes. For example, optional substituents are selected from one or more of lower alkyl, halo (in particular fluoro), lower alkoxy, nitro, cyano, hydroxy, amino, silyl-substituted alkyl and thio-substituted alkyl and protected forms thereof.

The term "silyl-substituted alkyl" as used herein refers to a lower alkyl group in which one or more of the carbon atoms is replaced with a Si atom and/or the lower alkyl group is substituted (i.e. one of more of the hydrogen atoms are replaced) with one or more silyl groups. The silicon atom is substituted as needed to fulfill valencey requirements, with one or more H atoms, lower alkyl groups and/or phenyl groups.

The term "thio-substituted alkyl" as used herein refers to a lower alkyl group in which one or more of the carbon atoms is replaced with an S atom and/or the lower alkyl group is substituted (i.e. one of more of the hydrogen atoms are replaced) with one or more thio groups. The sulfur atom is substituted as needed to fulfill valency requirements, with one or more H atoms, lower alkyl groups and/or phenyl groups.

The term "functional group that can be converted to $CO_2Et$" as used herein refers to any group that, when reacted under specific conditions, is chemically transformed into a $CO_2Et$ group. The specific conditions are those that do not degrade or decompose the remaining portions of the molecule during the chemical transformation. Suitably the group is converted to $CO_2Et$ in one or two chemical transformations. For example, a functional group that can be converted to $CO_2Et$ includes those groups that, when treated with a base or acid catalyst in ethanol, for example an ethoxide salt, such as sodium ethoxide, in ethanol, is converted to $CO_2Et$. A person skilled in the art that would understand that there are enumerable ester groups that, when treated with a base in ethanol, are converted to $CO_2Et$. These include, for example, but not limited to, aryl and heteroaryl, esters, lower and higher alkyl esters, thio esters, allyl esters, propargyl esters, and various substituted derivatives thereof. Also included within the definition of "functional group that can be converted to $CO_2Et$" are, for example but not limited to, C(O)H, C(O)OH, $C(O)O^-$, $CCl_3$, CN, C≡CH, $CH_2C$≡CH, $CH_2OH$ and various alkyl, aryl or heteroaryl ethers thereof, vinyl, $C(O\text{-alkyl})_3$, amides, alkyl amides, aryl amides, heteroaryl amides, thioesters, and heterocycles (such as thiazole, oxazole, thiophene, imidazole and the like). A person skilled in the art would be able to identify reagents that are suitable for the chemical transformation of these groups to $CO_2Et$.

The term "group that is removed under reduction or hydrogenation reaction conditions" as used herein refers to any group that when treated under reduction or hydrogenation reaction conditions is removed from the compounds of formula IV to generate a primary amine. The reduction or hydrogenation reaction conditions are those that do not degrade or decompose the remaining portions of the molecule during the reduction or hydrogenation and can be selected by a person skilled in the art. In an embodiment, the group that is removed under reduction or hydrogenation reaction conditions is incorporated into the compounds of formula IV by reaction of the compounds of formula III with ammonia or an ammonia derivative. Examples of groups that are removed under reduction or hydrogenation reaction conditions, include but are not limited to, OH, R, O—R, O(C)—R, $Si(R)_3$, $NO_2$, $NH_2$, $N(R)_2$, $S(O)_2R$, $S(O)_2OR$, $OS(O)_2R$, wherein each R is, independently alkyl, aryl or heteroaryl, and various substituted derivatives thereof.

The term "reduction conditions" as used herein means the use of a reducing agent that does not degrade or decompose the remaining portions of the molecule and such conditions can be selected by a person skilled in the art. Examples of suitable reducing conditions, include but are not limited to, metal hydrides, boranes, borohydrides, allanes, diimides, electrochemical reduction and single electron transfer.

The term "hydrogenation conditions" as used here means the use of hydrogen gas and/or another source of hydrogen and a suitable catalyst the conditions being such that they do not degrade or decompose the remaining portions of the molecule. Such conditions can be selected by a person skilled in the art. Examples of suitable hydrogenation conditions, include but are not limited to, $H_2$ gas and various metal catalysts (for example rhodium, ruthenium, aluminum, palladium, osmium and/or iron based catalysts) in a alcoholic solvent (for example ethanol and/or methanol).

The term "isotopic label" as used herein refers an isotopic form of an atom that is other than the most abundant form of that atom in nature. For example isotopic labels of $^{12}C$ atoms include $^{14}C$ and/or $^{13}C$ atom, isotopic labels of $^1H$ atoms include $^2H$ and/or $^3H$ atom, and an isotopic label of $^{14}N$ atoms is $^{15}N$. In some cases, the isotope is a radioisotope. In an embodiment of the application, an isotopic labeled compound is prepared using standard methods known in the art. For example, deuterium or tritium is incorporated into a compound using standard techniques, for example by hydrogenation of a suitable precursor using deuterium or tritium gas and a catalyst. Alternatively, a compound containing radioactive iodo is prepared from the corresponding trialkyltin (suitably trimethyltin) derivative using standard iodination conditions, such as [$^{125}$I] sodium iodide in the presence of chloramine-T in a suitable solvent, such as dimethylformamide. In a further embodiment, the trialkyltin compound is prepared from the corresponding non-radioactive halo, suitably iodo, compound using standard palladium-catalyzed stannylation conditions, for example hexamethylditin in the presence of tetrakis(triphenylphosphine) palladium (0) in an inert solvent, such as dioxane, and at elevated temperatures, suitably 50-100° C.

The terms "protective group" or "protecting group" or "PG" or the like as used herein refer to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3$^{rd}$ Edition, 1999 and in Kocienski, P. Protecting Groups, 3rd Edition, 2003, Georg Thieme Verlag (The Americas). Examples of suitable protecting groups include but are not limited to t-BOC, Ts, Ms, TBDMS, TBDPS, Tf, Bn, allyl, Fmoc, $C_{1-16}$acyl and the like. An example of suitable acid labile protecting group (i.e. a protecting group that is removed by treatment with acid), is t-BOC.

The term "protecting group reagent" as used herein refers to a protecting group precursor compound that reacts with a functional group in a target molecule to attach a protecting group to that group. In many cases, the protecting group reagent will comprise more than one compound, for example, the precursor to the protecting group and another reagent, such a base or an acid, that facilitates the reaction of the functional group with the protecting group precursor compound. Examples of protecting group reagents include, but are not limited to, a compound of the formula Pg-Lg, wherein Pg is a protecting group and Lg is a leaving group, such as t-butoxycarbonylanhydride ($BOC_2O$), Ts-Cl, Ms-Cl, TBDMS-Cl, TBDPS-Cl, $Tf_2O$, BnCl, BnBr, Tf-Cl and Fmoc-Cl.

The term "leaving group" of "Lg" as used herein refers to a group that is readily displaceable by a nucleophile, for example, under nucleophilic substitution reaction conditions. Examples of suitable leaving groups include, halo, Ms, Ts, Ns, Tf, Bn, $C_{1-6}$acyl, $OC_{1-16}$alkyl, alkylsulphonyl and the like.

The term "suitable", as in for example, "suitable protecting group", "suitable leaving group" or "suitable reaction conditions" means that the particular group or reaction conditions are selected to be compatible with the specific synthetic manipulation to be performed, and the identity of the molecule to be transformed, and this selection would be well within the skill of a person trained in the art. All process steps described herein are to be conducted under conditions suitable to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

t-BOC as used herein refers to the group t-butyloxycarbonyl.

Ac as used herein refers to the group acetyl.

Ts (tosyl) as used herein refers to the group p-toluenesulfonyl

Ms as used herein refers to the group methanesulfonyl

TBDMS as used herein refers to the group t-butyldimethylsilyl.

TBDPS as used herein refers to the group t-butyldiphenylsilyl.

Tf as used herein refers to the group trifluoromethanesulfonyl.

Ns as used herein refers to the group naphthalene sulphonyl.

Bn as used herein refers to the group benzyl.

Fmoc as used here refers to the group fluorenylmethoxycarbonyl.

In all of the compounds disclosed herein, that is compounds of the formulae I-VI, one or more, including all, of the hydrogen atoms is/are optionally replaced with F. A person skilled in the art would appreciate that only those hydrogens available for substitution by fluorine would be replaceable by fluorine.

In embodiments of the application, the compounds described herein have at least one asymmetric centre. Where compounds possess more than one asymmetric centre, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (e.g. less than 20%, suitably less than 10%, more suitably less than 5%) of compounds of the application having alternate stereochemistry.

The term "pharmaceutically acceptable" means compatible with the treatment of animals, in particular, humans.

The term "pharmaceutically acceptable salt" means an acid addition salt or a basic addition salt of a neutral compound, which is suitable for, or compatible with, the treatment of patients.

The term "pharmaceutically acceptable acid addition salt" as used herein means any non-toxic organic or inorganic salt of any base compound, or any of its intermediates. Illustrative inorganic acids, which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of the compounds of the application are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of the compounds of the application, for laboratory use, or for subsequent conversion to a pharmaceutically acceptable acid addition salt. In embodiments of the application, the pharmaceutically acceptable acid addition salt is the hydrochloride salt, or the $H_3PO_4$ salt. The formation of a desired compound salt is achieved using standard techniques. For example, the neutral compound is treated with an acid or base in a suitable solvent and the formed salt is isolated by filtration, extraction or any other suitable method.

The term "pharmaceutically acceptable basic addition salt" as used herein means any non-toxic organic or inorganic salt of any acid compound, or any of its intermediates. If a compound comprises an acidic group, for example a carboxylic acid, a basic addition salt is formed by adding a suitable base. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline, alkylammonias or ammonia. Such salts may exist in either a hydrated, solvated or substantially anhydrous form. The selection of the appropriate salt will be known to one skilled in the art. In an embodiment of the application, the pharmaceutically acceptable basic addition salt is an alkali metal salt, such as a sodium salt.

The term "solvate" as used herein means a compound or a pharmaceutically acceptable salt of a compound, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions.

The term "prodrugs" as used herein means functional derivatives of a compound which are readily convertible in vivo into the compound from which it is notionally derived. In an embodiment, prodrugs are conventional esters formed with available hydroxy, carboxylic acid and/or amino groups. For example, an available OH and/or nitrogen in a compound is acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters. In certain instances, the prodrugs are those in which one or more of the carboxylate or hydroxy groups in the compound is masked as groups which can be converted to carboxylate or hydroxy groups, respectively, in vivo. Conventional procedures for the selection and preparation of suitable prodrugs are described, for example, in "Design of Prodrugs" ed. H. Bundgaard, Elsevier, 1985.

The term "and/or" as used herein is meant to indicate that the listed options are either present together or individually. For example, the expression "pharmaceutically acceptable salt, solvate, prodrug and/or stereoisomer thereof" means that the compound can be a salt or a solvate or a prodrug or a stereoisomer of the referenced compound, or the compound can be compound can be a salt and a solvate and a prodrug and a stereoisomer of the referenced compound. For example, solvates of salts are alternate forms of compounds that are well known in the art.

To "inhibit" or "suppress" or "reduce" a function or activity, is to reduce the function or activity when compared to otherwise same conditions except for a condition or parameter of interest, or alternatively, as compared to another condition. The terms "inhibitor" and "inhibition", in the context of the present application, are intended to have a broad meaning and encompass compounds which directly or indirectly (e.g., via reactive intermediates, metabolites and the like) act on the influenza virus or symptoms thereof.

The term an "effective amount" or a "sufficient amount" of a compound as used herein is that amount sufficient to effect beneficial or desired results, including clinical results, and, as such, an "effective amount" depends upon the context in which it is being applied. For example, in the context of administering an agent that treats or prevents influenza, an effective amount of an agent is, for example, an amount sufficient to achieve a reduction in the amount of virus or of influenza symptoms as compared to the response obtained without administration of the agent.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder.

The term "subject" as used herein includes all members of the animal kingdom including human. The subject is preferably a human.

The terms "a," "an," or "the" as used herein not only include aspects with one member, but also includes aspects with more than one member. For example, an embodiment including "a solvent" should be understood to present certain aspects with one solvent or two or more additional solvents.

In compositions or reactions comprising an "additional" or "second" component, the second component as used herein is chemically different from the other components or first component. A "third" component is different from the other, first, and second components, and further enumerated or "additional" components are similarly different.

The term "reagent" as used herein indicates a compound or mixture of compounds that, when added to a reaction, tend to produce a particular effect on the substrate (reactant).

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

(II) Processes of the Application

The present application includes a process for the preparation of a compound of formula I:

I

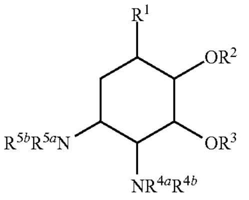

wherein $R^1$ is $CO_2Et$ or a functional group that can be converted to $CO_2Et$;

$R^2$ and $R^3$ are independently, suitable protecting groups, or $R^2$ and $R^3$ are joined to form a suitable protecting group;

$R^{4a}$ and $R^{4b}$ are independently selected from H and a suitable protecting group or $R^{4a}$ and $R^{4b}$ are joined to form a suitable protecting group;

$R^{5a}$ and $R^{5b}$ are independently selected from H and a suitable protecting group or $R^{5a}$ and $R^{5b}$ are joined to form a suitable protecting group; the process comprising:

(i) treating a compound of the formula II, wherein $R^1$, $R^2$, $R^3$, $R^{4a}$ and $R^{4b}$ are as defined in formula I under conditions for the [3,3] oxidative rearrangement of the allylic alcohol to provide a compound of the formula III, wherein $R^1$, $R^2$, $R^3$, $R^{4a}$ and $R^{4b}$ are as defined in formula I,

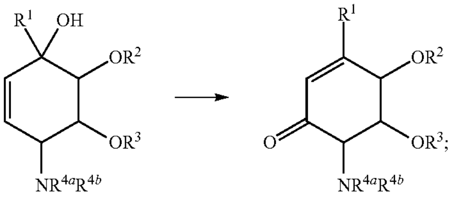

II III (ii) converting the compound of the formula III, wherein $R^1$, $R^2$, $R^3$, $R^{4a}$ and $R^{4b}$ are as defined in formula I, to a compound of the formula IV, wherein $R^1$, $R^2$, $R^3$, $R^{4a}$ and $R^{4b}$ are as defined in formula I and $R^7$ is a group that is removed under reduction or hydrogenation reaction conditions or $R^7$ is a suitable acid labile protecting group,

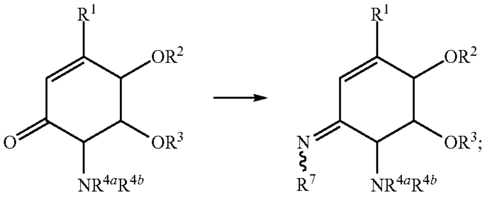

III IV and (iii) reducing or hydrogenating the compound of the formula IV, optionally in the presence of a suitable protecting group reagent, to provide compounds of the formula I, wherein:

(a) $R^{5a}$ and $R^{5b}$ are H when $R^7$ is a group that is removed under reduction or hydrogenation reaction conditions and the suitable protecting group reagent is not present;

(b) one of $R^{5a}$ and $R^{5b}$ is H and the other is a suitable protecting group or $R^{5a}$ and $R^{5b}$ are joined to form a suitable protecting group when $R^7$ is a group that is removed under reduction or hydrogenation reaction conditions and the suitable protecting group reagent is present; or (c) one of $R^{5a}$ and $R^{5b}$ is H and the other is a suitable acid labile protecting group when $R^7$ is a suitable acid labile protecting group,

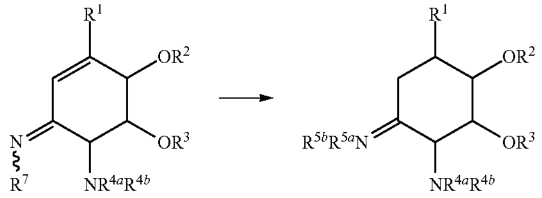

IV I wherein, in the compounds of the formulae I, II, III and/or IV, one or more available hydrogens in $R^1$, $R^2$, $R^3$, $R^{4a}$, $R^{4b}$, $R^{5a}$, $R^{5b}$ and/or $R^7$ is/are optionally replaced with F and/or one or more of available atoms in the compounds of the formulae I, II, III and/or IV is/are optionally replaced with an isotopic label.

It is an embodiment of the present application that the conditions for the [3,3] oxidative rearrangement of the allylic alcohol to provide a compound of the formula III metal oxidizing agents or halogen based oxidizing agents. Examples of such oxidizing agents include, but are not limited to chromium trioxide, chromate salts, dichromate salts, permanganate salts, manganate salts, bromine chlorine, fluorine and iodine. Examples of conditions for the [3,3] oxidative rearrangement of the allylic alcohol to provide a compound of the formula III are also described in Lizzio, F. A. Org. React. 1998, 53, 1 and Duaben, W. G.; Michno, D. M. J. Org. Chem. 1977, 42, 682. In an embodiment, the oxidizing agent is chromium trioxide. In a further embodiment, the chromium trioxide is prepared by dissolving chromium trioxide in acetic anhydride under conditions to obtain a homogeneous solution, for example at a temperature of about 50° C. to about 100° C., about 70° C. to about 90° C., or about 80° C. In a further embodiment the conditions for the [3,3] oxidative rearrangement comprise a temperature of about −20° C. to about 20° C., about −10° C. to about 10° C., or at about 4° C. or 5° C., followed by warming to room temperature, in a suitable organic solvent, such as dichloromethane.

In another embodiment of the present application, the compound of the formula III is converted to an oxime, imine or hydrazone of the formula IV by reaction with a suitable ammonia derivative, to provide compounds of formula IV, wherein $R^7$ is selected from R, O—R, OH, NH(alkyl), N(alkyl)(alkyl), $NH_2$, $Si(R)_3$, $S(O)_2R$, $SO_2OR$ and $OS(O)_2R$ wherein each R is, independently, optionally substituted alkyl, optionally substituted aryl or optionally substituted heteroaryl. In an embodiment, alkyl is lower alkyl and aryl is phenyl. In a further embodiment, $R^7$ is OH.

In another embodiment of the present application, the compound of the formula III is converted to the oxime of the formula IV by reacting the compound of formula III with hydroxylamine, for example hydroxy amine hydrochloride, at a temperature of about −20° C. to about 20° C., about −10° C. to about 10° C., or at about 0° C., followed by warming to room temperature, in a suitable organic solvent, such as dichloromethane.

In a further embodiment of the application, the compound of the formula IV is reduced using hydrogenation conditions, for example in the presence of hydrogen gas and one or more metal catalysts in a solvent, such as ethanol and water at elevated pressure and at about room temperature.

It is an embodiment of the application that the suitable protecting group reagent is t-butoxycarbonylanhydride $[(BOC)_2O]$ or the suitable acid-labile protecting group is t-BOC.

It is an embodiment of the application that $R^1$ in the compounds of the formulae I-IV is $CO_2C_{1-3}$alkyl. In a further embodiment $R^1$ in the compounds of the formulae I-IV is $CO_2Me$, $CO_2Et$, $CO_2iPr$, $CO_2nPr$ or $CO_2CH_2C{\equiv}CH$. In a further embodiment, $R^1$ in the compounds of the formulae I-IV is $CO_2Et$.

It is another embodiment of the application that $R^2$ and $R^3$ in the compounds of formulae I-IV are linked to form, together with the atoms to which they are attached, a 5-membered ring that is substituted with one or two methyl or ethyl groups. It is another embodiment of the application that $R^2$ and $R^3$ in the compounds of formulae I-IV are linked to form, together with the atoms to which they are attached, a 2,2-dimethyl-1,3-dioxolane ring.

In a further embodiment of the application one of $R^{4a}$ and $R^{4b}$ in the compounds of formulae I-IV is $C_{1-4}$acyl and the other is H. In a another embodiment one of $R^{4a}$ and $R^{4b}$ in the compounds of formulae I-IV is C(O)Me or C(O)Et, suitably C(O)Me, and the other is H.

In another embodiment of the present application, one of $R^{5a}$ and $R^{5b}$ in the compounds of formulae I-IV is H or t-butoxycarbonyl, and the other is H.

In an embodiment of the application, the compounds of formula II are prepared using methods known in the art. For example, compounds of formula II are prepared as described in Hudlicky, T. PCT Patent Application No. PCT/CA20009/000622, May 12, 2009 or Sullivan, B.; Carrera, I.; Drouin, M.; Hudlicky, T. *Angew. Chem. Int. Ed.* 2009, 48, 4229-4231.

In an embodiment of the application, the compounds of formula II are derived from cis-dihydrodiols of benzoate esters. These latter compounds are readily available via the enzymatic dihydroxylation of benzoate esters using, for example, *E. coli* JM 109(pDTG 601) strain in a whole-cell fermenation as described in Fabris, F.; Collins, J.; Sullivan, B.; Leisch, H.; Hudlicky, T. *Org. Biomol. Chem.* 2009, 7, 2619-2627. A wide variety of benzoate esters can be used to make a chiral cis-diol. At certain stages of the synthesis these esters can be treated with, for example, ethanol/ethoxide or ethanol/acid catalyst and converted to the ethyl ester.

It is an embodiment of the present application that the stereochemistry in the compounds of the formulae I, II, III and/or IV is that found in oseltamivir. Accordingly, the present application also includes a process for the preparation of a compound of formula I:

I

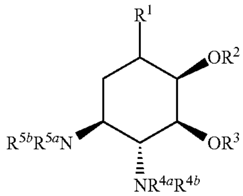

wherein $R^1$ is $CO_2Et$ or a functional group that can be converted to $CO_2Et$;

$R^2$ and $R^3$ are independently, suitable protecting groups, or $R^2$ and $R^3$ are joined to form a suitable protecting group;

$R^{4a}$ and $R^{4b}$ are independently selected from H and a suitable protecting group or $R^{4a}$ and $R^{4b}$ are joined to form a suitable protecting group;

$R^{5a}$ and $R^{5b}$ are independently selected from H and a suitable protecting group or $R^{5a}$ and $R^{5b}$ are joined to form a suitable protecting group; the process comprising:

(i) treating a compound of the formula II, wherein $R^1$, $R^2$, $R^3$, $R^{4a}$ and $R^{4b}$ are as defined in formula I under conditions for the [3,3] oxidative rearrangement of the allylic alcohol to provide a compound of the formula III, wherein $R^1$, $R^2$, $R^3$, $R^{4a}$ and $R^{4b}$ are as defined in formula I,

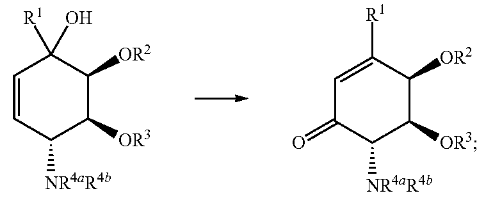

II III (ii) converting the compound of the formula III, wherein $R^1$, $R^2$, $R^3$, $R^{4a}$ and $R^{4b}$ are as defined in formula I, to a compound of the formula IV, wherein $R^1$, $R^2$, $R^3$, $R^{4a}$ and $R^{4b}$ are as defined in formula I and $R^7$ is a group that is removed under reduction or hydrogenation reaction conditions or $R^7$ is a suitable acid labile protecting group,

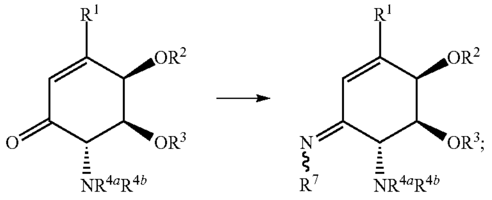

III IV and (iii) reducing or hydrogenating the compound of the formula IV, optionally in the presence of a suitable protecting group reagent, to provide compounds of the formula I, wherein:

(a) $R^{5a}$ and $R^{5b}$ are H when $R^7$ is a group that is removed under reduction or hydrogenation reaction conditions and the suitable protecting group reagent is not present;

(b) one of $R^{5a}$ and $R^{5b}$ is H and the other is a suitable protecting group or $R^{5a}$ and $R^{5b}$ are joined to form a suitable protecting group when $R^7$ is a group that is removed under reduction or hydrogenation reaction conditions and the suitable protecting group reagent is present; or (c) one of $R^{5a}$ and $R^{5b}$ is H and the other is a suitable acid labile protecting group when $R^7$ is a suitable acid labile protecting group,

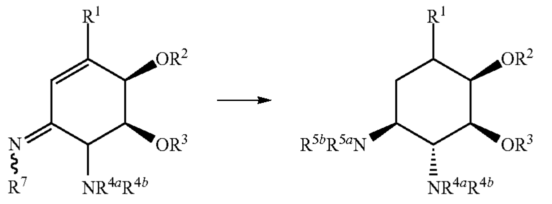

IV I wherein, in the compounds of the formulae I, II, III and/or IV, one or more available hydrogens in $R^1$, $R^2$, $R^3$, $R^{4a}$, $R^{4b}$, $R^{5a}$, $R^{5b}$ and/or $R^7$ is/are optionally replaced with F and/or one or more of available atoms in the compounds of the formulae I, II, III and/or IV is/are optionally replaced with an isotopic label.

It is important to note that, while the relative and/or absolute stereochemistry of the compounds of formula I, II, III and/or IV is as shown above, it is an embodiment that these compounds exist as mixtures containing from about 0% to about 50%, about 1% to about 40%, about 2% to about 30%, about 3% to about 20%, about 4% to about 10% or about 5%, of compounds having alternate stereochemistry.

Compounds of formula I are converted to oseltamivir using methods known in the art. For example, a compound of the formula I is treated under conditions to provide compounds of the formula V:

V

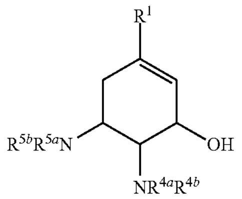

for example as described in Sullivan, B.; Carrera, I.; Drouin, M.; Hudlicky, T. *Angew. Chem. Int. Ed.* 2009, 48, 4229-4231. Compounds of formula V are converted to oseltamivir, for example, as described in Yamatsugu, K.; Yin, L.; Kamijo, S.; Kimura, Y.; Kanai, M.; Shibasaki, M. *Angew. Chem. Int. Ed.* 2009, 48, 1070 and in Sungwoo Hong, Y.; Corey, E. J. *J. Am. Chem. Soc.* 2006, 128, 6310.

(III) Compounds of the Application

Also within the scope of the present application are novel intermediate compounds for the preparation of oseltamivir and analogs thereof. Accordingly, the application includes compounds of formula III:

III

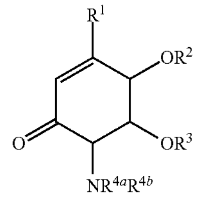

wherein $R^1$ is $CO_2Et$ or a functional group that can be converted to $CO_2Et$;

$R^2$ and $R^3$ are independently selected from H and a suitable protecting group, or $R^2$ and $R^3$ are joined to form a suitable protecting group; and $R^{4a}$ and $R^{4b}$ are independently selected from H and a suitable protecting group or $R^{4a}$ and $R^{4b}$ are joined to form a suitable protecting group;

wherein, one or more available hydrogens in $R^1$, $R^2$, $R^3$, $R^{4a}$ and/or $R^{4b}$ is/are optionally replaced with F and/or one or more of available atoms is/are optionally replaced with an isotopic label, or a salt and/or solvate thereof.

The application also includes compounds of formula IV:

IV

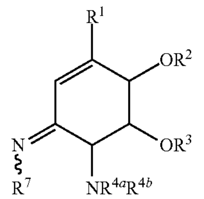

wherein $R^1$ is $CO_2Et$ or a functional group that can be converted to $CO_2Et$;

$R^2$ and $R^3$ are independently selected from H and a suitable protecting group, or $R^2$ and $R^3$ are joined to form a suitable protecting group;

$R^{4a}$ and $R^{4b}$ are independently selected from H and a suitable protecting group or $R^{4a}$ and $R^{4b}$ are joined to form a suitable protecting group; and $R^7$ is a group that is removed under reduction or hydrogenation reaction conditions or $R^7$ is a suitable acid labile protecting group, wherein, one or more available hydrogens in $R^1$, $R^2$, $R^3$, $R^{4a}$, $R^{4b}$ and/or $R^7$ is/are optionally replaced with F and/or one or more of available atoms is/are optionally replaced with an isotopic label, or a salt, solvate and/or prodrug thereof.

It is an embodiment of the application that $R^1$ in the compounds of the formula III or IV is $CO_2C_{1-3}$alkyl. In a further embodiment $R^1$ in the compounds of the formulae III or IV is $CO_2Me$, $CO_2Et$, $CO_2iPr$, $CO_2nPr$, or $CO_2CH_2C{\equiv}CH$. In a further embodiment, $R^1$ in the compounds of the formulae I-IV is $CO_2Et$.

It is another embodiment of the application that $R^2$ and $R^3$ in the compounds of formula III or IV are linked to form, together with the atoms to which they are attached, a 5-membered ring that is substituted with one or two methyl or ethyl groups. It is another embodiment of the application that $R^2$ and $R^3$ in the compounds of formulae I-IV are linked to form, together with the atoms to which they are attached, a 2,2-dimethyl-1,3-dioxolane ring.

In a further embodiment of the application one of $R^{4a}$ and $R^{4b}$ in the compounds of formula III or IV is $C_{1-4}$acyl and the other is H. In a another embodiment one of $R^{4a}$ and $R^{4b}$ in the compounds of formula III or IV is C(O)Me or C(O)Et, suitably C(O)Me, and the other is H.

In another embodiment of the present application, one of $R^{5a}$ and $R^{5b}$ in the compounds of formula III is H or t-butoxycarbonyl, and the other is H.

In another embodiment, $R^7$ in the compounds of formula IV is selected from R, O—R, OH, NH(alkyl), N(alkyl)(alkyl), $NH_2$ and $Si(R)_3$, wherein each R is, independently, optionally substituted alkyl or optionally substituted aryl. In an embodiment, alkyl is lower alkyl and aryl is phenyl. In a further embodiment, $R^7$ is OH.

It is an embodiment of the present application that the stereochemistry in the compounds of the formula III or IV is that found in oseltamivir. Accordingly, the present application also includes a compound of the formula III,

III

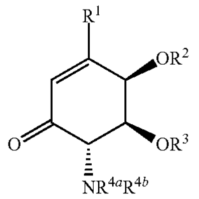

wherein $R^1$, $R^2$, $R^3$, $R^{4a}$ and $R^{4b}$ are as defined above, or a salt and/or solvate thereof, or a compound of formula IV:

IV

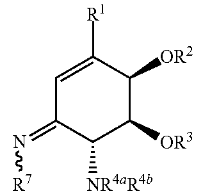

wherein $R^1$, $R^2$, $R^3$, $R^{4a}$, $R^{4b}$ and $R^7$ are as defined above, or a salt, solvate and/or prodrug thereof, wherein, one or more available hydrogens in $R^1$, $R^2$, $R^3$, $R^{4a}$, $R^{4b}$ and/or $R^7$ is/are optionally replaced with F and/or one or more of available atoms is/are optionally replaced with an isotopic label, In an embodiment, the compound of formula III is (3aR,7S,7aS)-ethyl-7-acetamido-2,2-dimethyl-6-oxo-3a,6,7,7a-tetrahydrobenzo[d][1,3]dioxole-4-carboxylate (compound 7), or a solvate thereof.

In an embodiment, the compound of formula IV is (3aR,7R,7aS)-ethyl-7-acetamido-6-(hydroxyimino)-2,2-dimethyl-3a,6,7,7a-tetrahydrobenzo[d][1,3]dioxole-4-carboxylate (compound 8), or a solvate thereof.

Certain compounds disclosed herein have been shown to have antiviral activity. Accordingly, the present application also includes a compound of formula V:

V

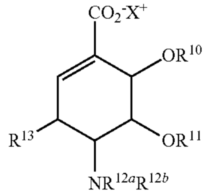

wherein $R^{10}$ and $R^{11}$ are independently selected from H, $C_{1-6}$alkyl and $C_{1-6}$acyl, or $R^{10}$ and $R^{11}$ are joined, together with the atoms to which they are attached, to form a 5-10-membered ring that is unsubstituted or substituted with one or more of halo or $C_{1-6}$alkyl;

$R^{12a}$ and $R^{12b}$ are independently selected from H, $C_{1-6}$alkyl and $C_{1-6}$acyl;

$R^{13}$ is selected from $OR^{14}$ and $NR^{15a}R^{15b}$ or $R^{13}$ is =O or =$NR^{16}$;

$R^{14}$ is selected from H, $C_{1-6}$alkyl and $C_{1-6}$acyl;

$R^{15a}$ and $R^{15b}$ are independently selected from H, $C_{1-6}$alkyl and $C_{1-6}$acyl;

$R^{16}$ is selected from H, OH, $C_{1-6}$alkyl, $OC_{1-6}$alkyl, $C_{1-6}$acyl, $OC_{1-6}$acyl, $NH_2$, $NHC_{1-6}$alkyl, $N(C_{1-6}alkyl)(C_{1-6}alkyl)$ and $NHC_{1-6}$acyl, or $R^{16}$ and one of $R^{12a}$ and $R^{12b}$ form a linker group "-A-C(O)-" to provide a compound of the formula:

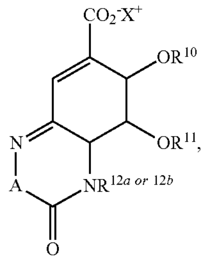

wherein A is O or NH;

$X^+$ is a cation; and one or more available hydrogens in $R^{10}$, $R^{11}$, $R^{12a}$, $R^{12b}$, $R^{13}$, $R^{14}$, $R^{15a}$, $R^{15a}$, $R^{15b}$ and/or $R^{16}$ is/are optionally replaced with F and/or one or more of available atoms in the compounds of the formula is/are optionally replaced with an isotopic label, or a pharmaceutically acceptable salt and/or solvate thereof.

In an embodiment of the application, $R^{10}$ and $R^{11}$ are independently selected from H, $C_{1-4}$alkyl and $C_{1-4}$acyl, or $R^{10}$ and $R^{11}$ are joined, together with the atoms to which they are attached, to form a 5-6-membered ring that is unsubstituted or substituted with one or more of halo or $C_{1-4}$alkyl. In another embodiment of the application, $R^{10}$ and $R^{11}$ are independently selected from H, Me, Et, C(O)Me and C(O)Et, or $R^{10}$ and $R^{11}$ are joined, together with the atoms to which they are attached, to form a 5-6-membered ring that is unsubstituted or substituted with one or two Me or Et. In another embodiment of the application, $R^{10}$ and $R^{11}$ are joined, together with the atoms to which they are attached, to form a 5-membered ring that is unsubstituted or substituted with one or two Me.

In an embodiment of the application, $R^{12a}$ and $R^{12b}$ are independently selected from H, $C_{1-4}$alkyl and $C_{1-4}$acyl. In another embodiment of the application, $R^{12a}$ and $R^{12b}$ are independently selected from H, Me, Et, C(O)Me and C(O)Et.

In another embodiment, one of $R^{12a}$ and $R^{12b}$ is H and the other is selected from Me, Et, C(O)Me and C(O)Et. In another embodiment, one of $R^{12a}$ and $R^{12b}$ is H and the other is selected from C(O)Me and C(O)Et.

In an embodiment of the application $R^{13}$ is selected from $OR^{14}$ or $R^{13}$ is $=NR^{16}$, where $R^{14}$ is selected from H, $C_{1-4}$alkyl and $C_{1-4}$acyl and $R^{16}$ is selected from H, OH, $C_{1-4}$alkyl, $OC_{1-4}$alkyl, $C_{1-4}$acyl, $OC_{1-4}$acyl $NH_2$, $NHC_{1-4}$ alkyl, $N(C_{1-4}alkyl)(C_{1-4}alkyl)$ and $NHC_{1-4}$acyl. In another embodiment of the application $R^{13}$ is selected from $OR^{14}$ or $R^{13}$ is $=NR^{16}$, where $R^{14}$ is selected from H, Me, Et, C(O)Me and C(O)Et and $R^{16}$ is selected from H, OH, Me, Et, OMe, OEt, C(O)Me, C(O)Et, OC(O)Me, OC(O)Et, $NH_2$, NHMe, NHEt, $N(Me)_2$, $N(Et)_2$, NHC(O)Me and NH(C(O)Et. In another embodiment of the application $R^{13}$ is selected from OH, OC(O)Me, =N—OC(O)Me and =N—OH.

In an embodiment of the application, $R^{16}$ and one of $R^{12a}$ and $R^{12b}$ form a linker group "-A-C(O)-" to provide a compound of the formula:

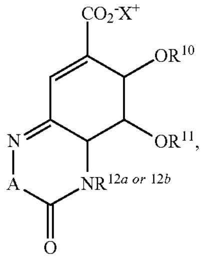

wherein A is O.

In an embodiment, $X^+$ is an alkali metal cation. In a further embodiment, $X^+$ is $Na^+$, $K^+$ or $Li^+$. In another embodiment $X^+$ is a cation is $Na^+$.

In a specific embodiment of the present application there is also included a compound of formula V:

V

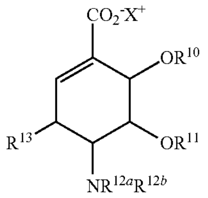

wherein $R^{10}$ and $R^{11}$ are independently selected from H, $C_{1-6}$alkyl and $C_{1-6}$acyl, or $R^{10}$ and $R^{11}$ are joined, together with the atoms to which they are attached, to form a 5-10-membered ring that is unsubstituted or substituted with one or more of halo or $C_{1-6}$alkyl;

$R^{12a}$ and $R^{12b}$ are independently selected from H, $C_{1-6}$alkyl and $C_{1-6}$acyl;

$R^{13}$ is $=NR^{16}$;

$R^{16}$ is selected from H, OH, $C_{1-6}$alkyl, $OC_{1-6}$alkyl, $C_{1-6}$acyl, $OC_{1-6}$acyl, $NH_2$, $NHC_{1-6}$alkyl, $N(C_{1-6}alkyl)(C_{1-6}alkyl)$ and $NHC_{1-6}$acyl, or $R^{16}$ and one of $R^{12a}$ and $R^{12b}$ form a linker group "-A-C(O)-" to provide a compound of the formula:

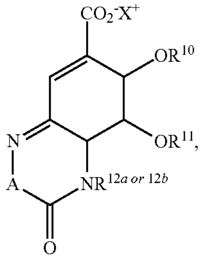

wherein A is O or NH;

$X^+$ is a cation; and one or more available hydrogens in $R^{10}$, $R^{11}$, $R^{12a}$, $R^{12b}$, $R^{13}$, $R^{14}$, $R^{15a}$, $R^{15b}$ and/or $R^{16}$ is/are optionally replaced with F and/or one or more of available atoms in the compounds of the formula is/are optionally replaced with an isotopic label, or a pharmaceutically acceptable salt, solvate and/or prodrug thereof.

In an embodiment of the application, the compound of formula V is: sodium (3aR,7R,7aS,E)-7-acetamido-6-(hydroxyimino)-2,2-dimethyl-3a,6,7,7a-tetrahydrobenzo[d][1,3]dioxole-4-carboxylate (compound 17) or an alternate pharmaceutically acceptable salt thereof and/or a solvate and/or prodrug thereof; or sodium (3aR,6R,7R,7aS)-7-acetamido-6-hydroxy-2,2-dimethyl-3a,6,7,7a-tetrahydrobenzo[d][1,3]dioxole-4-carboxylate (compound 19) or an alternate pharmaceutically acceptable salt thereof and/or a solvate thereof.

The present application also includes a compound of the formula VI:

VI

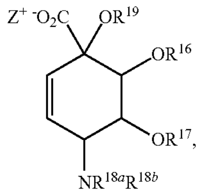

wherein $R^{16}$ and $R^{17}$ are independently selected from H, $C_{1-6}$alkyl and $C_{1-6}$acyl, or $R^{16}$ and $R^{17}$ are joined together to form, together with the atoms to which they are attached, a 5-10-membered ring that is unsubstituted or substituted with one or more of halo or $C_{1-4}$alkyl;

$R^{18a}$ and $R^{18b}$ are independently selected from H, $C_{1-6}$alkyl and $C_{1-6}$acyl;

$R^{19}$ is selected from H, $C_{1-6}$alkyl and $C_{1-6}$acyl;

$Z^+$ is a cation; and one or more available hydrogens in $R^{16}$, $R^{17}$, $R^{18a}$, $R^{18b}$ and/or $R^{19}$ is/are optionally replaced with F and/or one or more of available atoms in the compounds of the formula is/are optionally replaced with an isotopic label, or a pharmaceutically acceptable salt and/or solvate thereof.

In an embodiment of the application, $R^{16}$ and $R^{17}$ are independently selected from H, $C_{1-4}$alkyl and $C_{1-4}$acyl, or $R^{16}$ and $R^{17}$ are joined, together with the atoms to which they are attached, to form a 5-6-membered ring that is unsubstituted or substituted with one or more of halo or $C_{1-4}$alkyl. In another embodiment of the application, $R^{16}$ and $R^{17}$ are independently selected from H, Me, Et, C(O)Me and C(O)Et, or $R^{16}$ and $R^{17}$ are joined, together with the atoms to which they are attached, to form a 5-6-membered ring that is unsubstituted or substituted with one or two Me or Et. In another embodiment of the application, $R^{16}$ and $R^{17}$ are joined, together with the atoms to which they are attached, to form a 5-membered ring that is unsubstituted or substituted with one or two Me.

In an embodiment of the application, $R^{18a}$ and $R^{18b}$ are independently selected from H, $C_{1-4}$alkyl and $C_{1-4}$acyl. In another embodiment of the application, $R^{18a}$ and $R^{18b}$ are independently selected from H, Me, Et, C(O)Me and C(O)Et. In another embodiment, one of $R^{18a}$ and $R^{18b}$ is H and the other is selected from Me, Et, C(O)Me and C(O)Et. In another embodiment, one of $R^{18a}$ and $R^{18b}$ is H and the other is selected from C(O)Me and C(O)Et.

In an embodiment of the application, $R^{19}$ is selected from H, $C_{1-4}$alkyl and $C_{1-4}$acyl. In another embodiment, $R^{19}$ is selected from H, Me, Et, C(O)Me and C(O)Et. In another embodiment $R^{19}$ is H.

In an embodiment, $Z^+$ is an alkali metal cation. In a further embodiment, $Z^+$ is $Na^+$, $K^+$ or $Li^+$. In another embodiment $Z^+$ is a cation is $Na^+$.

In an embodiment of the application, the compound of formula VI is: sodium (3aS,4S,7R,7aS)-7-acetamido-4-hydroxy-2,2-dimethyl-3a,4,7,7a-tetrahydrobenzo[d][1,3]dioxole-4-carboxylate (compound 16) or an alternate pharmaceutically acceptable salt thereof and/or solvate thereof.

It is an embodiment of the present application that the stereochemistry in the compounds of the formula V or VI is that found in oseltamivir. Accordingly, the present application also includes a compound of the formula V, (V)

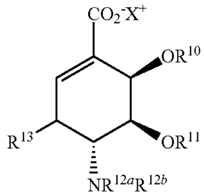

wherein $R^{10}$, $R^{11}$, $R^{12a}$, $R^{12b}$, $R^{13}$ and $X^+$ are as defined above, or a compound of formula IV:

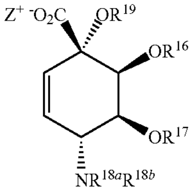

wherein $R^{16}$, $R^{16}$, $R^{18a}$, $R^{18b}$, $R^{19}$ and $Z^+$ are as defined above, wherein, one or more available hydrogens in $R^{10}$, $R^{11}$, $R^{12a}$, $R^{12b}$, $R^{13}$, $R^{16}$, $R^{16}$, $R^{18a}$, $R^{18b}$ and/or $R^{19}$ is/are optionally replaced with F and/or one or more of available atoms is/are optionally replaced with an isotopic label, or a pharmaceutically acceptable salt and/or solvate thereof.

In a specific embodiment of the present application there is also included a compound of formula V:

V

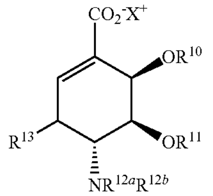

wherein $R^{16}$ and $R^{11}$ are independently selected from H, $C_{1-6}$alkyl and $C_{1-6}$acyl, or $R^{10}$ and $R^{11}$ are joined, together with the atoms to which they are attached, to form a 5-10-membered ring that is unsubstituted or substituted with one or more of halo or $C_{1-6}$alkyl;

$R^{12a}$ and $R^{12b}$ are independently selected from H, $C_{1-6}$alkyl and $C_{1-6}$acyl;

$R^{13}$ is $=NR^{16}$;

$R^{16}$ is selected from H, OH, $C_{1-6}$alkyl, $OC_{1-6}$alkyl, $C_{1-6}$acyl, $OC_{1-6}$acyl, $NH_2$, $NHC_{1-6}$alkyl, $N(C_{1-6}alkyl)(C_{1-6}alkyl)$ and $NHC_{1-6}$acyl, or $R^{16}$ and one of $R^{12a}$ and $R^{12b}$ form a linker group "-A-C(O)-" to provide a compound of the formula:

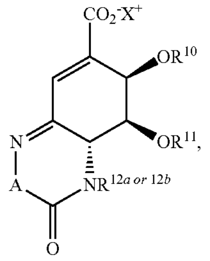

wherein A is O or NH;

$X^+$ is a cation; and one or more available hydrogens in $R^{10}$, $R^{11}$, $R^{12a}$, $R^{12b}$, $R^{13}$, $R^{14}$, $R^{15a}$, $R^{15b}$ and/or $R^{16}$ is/are optionally replaced with F and/or one or more of available atoms in the compounds of the formula is/are optionally replaced with an isotopic label, or a pharmaceutically acceptable salt, solvate and/or prodrug thereof.

In an embodiment of the application, the prodrug of a compound of formula V or VI is the corresponding acid, $C_{1-20}$alkyl ester, $C_{6-14}$aryl ester or $C_{1-6}$alkylene$C_{6-14}$aryl (e.g. benzyl) ester.

It is important to note that, while the relative and/or absolute stereochemistry of the compounds of formula III, IV, V and/or VI is as shown above, it is an embodiment that these compounds exist as mixtures containing from about 0% to about 50%, about 1% to about 40%, about 2% to about 30%, about 3% to about 20%, about 4% to about 10% or about 5%, of compounds having alternate stereochemistry.

The compounds of formula V and VI are available by treating the corresponding esters, for example ethyl esters (prepared using the processes of the present application), with a base, such an hydroxide, in aqueous alcohol, with optional heating as needed to drive the reaction to completion.

(IV) Compositions and Therapeutic Applications

As hereinbefore mentioned, novel compounds of the formulae III, IV, V and VI have been prepared. Accordingly, the present application includes all uses of the compounds of formulae III, IV, V and VI, including their use as intermediates in the preparation of oseltamivir as in therapeutic methods and compositions for treatment of influenza, their use in diagnostic assays and their use as research tools. In particular, the present application includes the use of one or more compounds of the formulae V or VI, or a pharmaceutically acceptable salt, solvate, prodrug and/or stereoisomer thereof, as a medicament, Another aspect of the application relates to a use of one or more compounds of the formula V or VI, or a pharmaceutically acceptable salt, solvate, prodrug and/or stereoisomer thereof, for the treatment or prevention of influenza.

Another aspect of the application relates to a use of one or more compounds of the formula V or VI, or a pharmaceutically acceptable salt, solvate, prodrug and/or stereoisomer thereof, for the preparation of a medicament for the treatment or prevention of influenza.

Another aspect of the application includes one or more compounds of the formula V or VI, or a pharmaceutically acceptable salt, solvate, prodrug and/or stereoisomer thereof, for use to treat or prevent of influenza.

Also within the scope of the present application is a method of treating or preventing influenza comprising administering an effective amount of one or more compounds of the formula V or VI, or a pharmaceutically acceptable salt, solvate, prodrug and/or stereoisomer thereof to a subject in need thereof.

In an aspect of the present application, the one or more compounds of the formula III or IV, or a salt, solvate and/or stereoisomer thereof, are formulated into compositions for example, for use as reagents in chemical transformations. Accordingly, the present application further includes a composition comprising one or more compounds of the formula III or IV, or a salt, solvate and/or stereoisomer thereof, and a carrier and/or diluent.

In an aspect of the present application, the one or more compounds of the formula V or VI, or a pharmaceutically acceptable salt, solvate, prodrug and/or stereoisomer thereof, are formulated into pharmaceutical compositions for administration to human subjects in a biologically compatible form suitable for administration in vivo. Accordingly, the present application further includes a pharmaceutical composition comprising one or more compounds of the formula V or VI, or a pharmaceutically acceptable salt, solvate, prodrug and/or stereoisomer thereof, and a pharmaceutically acceptable carrier and/or diluent.

The pharmaceutical compositions containing the one or more compounds of the formula V or VI, or a pharmaceutically acceptable salts, solvates, prodrugs and/or stereoisomers thereof, are prepared by known methods for the preparation of pharmaceutically acceptable compositions, which can be administered to subjects, such that an effective quantity of the active substance is combined in a mixture with a pharmaceutically acceptable vehicle. Suitable vehicles are described, for example, in Remington's Pharmaceutical Sciences (2000-20th edition) and in The United States Pharmacopeia: The National Formulary (USP 24 NF19) published in 1999). On this basis, the compositions include, albeit not exclusively, solutions of the substances in association with one or more pharmaceutically acceptable vehicles or diluents, and contained in buffered solutions with a suitable pH and iso-osmotic with the physiological fluids.

In an embodiment of the application, the one or more compounds of the formula V or VI, or a prodrug and/or stereoisomer thereof, are used in the form of the free base, in the form of salts and/or solvates. All forms are within the scope of the application.

In accordance with embodiments of the methods and uses of the application, the described one or more compounds, and salts, solvates, prodrugs and/or stereoisomers thereof are administered to a patient in a variety of forms depending on the selected route of administration, as will be understood by those skilled in the art. In an embodiment the one or more compounds are administered, for example, by oral, parenteral, buccal, sublingual, nasal, rectal, patch, pump or transdermal (topical) administration and pharmaceutical compositions formulated accordingly. Parenteral administration includes, for example, intravenous, intraperitoneal, subcutaneous, intramuscular, transepithelial, nasal, intrapulmonary, intrathecal, rectal and topical modes of administration. In an embodiment, parenteral administration is by continuous infusion over a selected period of time.

In a further embodiment, the one or more compounds are orally administered, for example, with an inert diluent or with an assimilable edible carrier, or are enclosed in hard or soft shell gelatin capsule, or are compressed into tablets, or are incorporated directly with the food of the diet. In another embodiment, for oral therapeutic administration, the one or more compounds are incorporated with excipient and used in the form of ingestible tablets, buccal tablets, troches, capsules, elixirs, suspensions, syrups, wafers, and the like.

In a further embodiment the one or more compounds are administered parenterally. In an embodiment, solutions of the one or more compounds are prepared in water suitably mixed with a surfactant such as hydroxypropylcellulose. In another embodiment, dispersions are prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (2000-20th edition) and in The United States Pharmacopeia: The National Formulary (USP 24 NF19) published in 1999.

The pharmaceutical forms suitable for injectable use include, for example, sterile aqueous solutions or dispersion and sterile powders for the extemporaneous preparation of sterile injectable solutions or dispersions. In all cases the form must be sterile and must be fluid to the extent that easy syringability exists. Ampoules are convenient unit dosages.

In another embodiment, compositions for nasal administration are formulated as aerosols, drops, gels or powders. Aerosol formulations typically comprise a solution or fine suspension of the one or more compounds in a physiologically acceptable aqueous or non-aqueous solvent and are usually presented in single or multidose quantities in sterile form in a sealed container, which can take the form of a cartridge or refill for use with an atomizing device. Alternatively, the sealed container is a unitary dispensing device such as a single dose nasal inhaler or an aerosol dispenser fitted with a metering valve, which is intended for disposal after use. Where the dosage form comprises an aerosol dispenser, it will contain a propellant, which is, for example, a compressed gas such as compressed air or an organic propellant such as fluorochlorohydrocarbon. In another embodiment, the aerosol dosage form take the form of a pump-atomizer.

Compositions suitable for buccal or sublingual administration include, for example, tablets, lozenges, and pastilles, wherein the one or more compounds are formulated with a carrier such as sugar, acacia, tragacanth, or gelatin and glycerine. Compositions for rectal administration are conveniently in the form of suppositories containing a conventional suppository base such as cocoa butter.

Compositions for topical administration include, for example, propylene glycol, isopropyl alcohol, mineral oil and/or glycerin. Preparations suitable for topical administration include, for example, liquid or semi-liquid preparations such as liniments, lotions, applicants, oil-in-water or water-in-oil emulsions such as creams, ointments or pastes; or solutions or suspensions such as drops. In addition to the aforementioned ingredients, the topical preparations optionally include one or more additional ingredients such as diluents, buffers, flavouring agents, binders, surface active agents, thickeners, lubricants, preservatives, e.g. methyl hydroxybenzoate (including anti-oxidants), emulsifying agents and the like.

In another embodiment, sustained or direct release compositions are formulated, e.g. liposomes or those wherein the one or more compounds are protected with differentially degradable coatings, such as by microencapsulation, multiple coatings, etc. It is also possible to freeze-dry the one or more compounds and use the lyophilizates obtained, for example, for the preparation of products for injection.

The dosage administered will vary depending on the use and known factors such as the pharmacodynamic characteristics of the particular compound(s), and its mode and route of administration; age, health, and weight of the individual recipient; nature and extent of symptoms, kind of concurrent treatment, frequency of treatment, and the effect desired.

The following non-limiting examples are illustrative of the present application:

EXAMPLES

The compound numbers referred to in the following Examples are those shown in Scheme 2. It should be noted that the yields reported in Scheme 2 and in the experimental examples reported hereinbelow are non-limiting, unoptimized yields. A person skilled in the art would appreciate that reaction conditions will vary depending on a number of factors, including, for example, reaction scale and atmospheric conditions. The present application extends to processes that provide yields (greater or less) of the desired products that are other than those reported hereinbelow.

Scheme 2

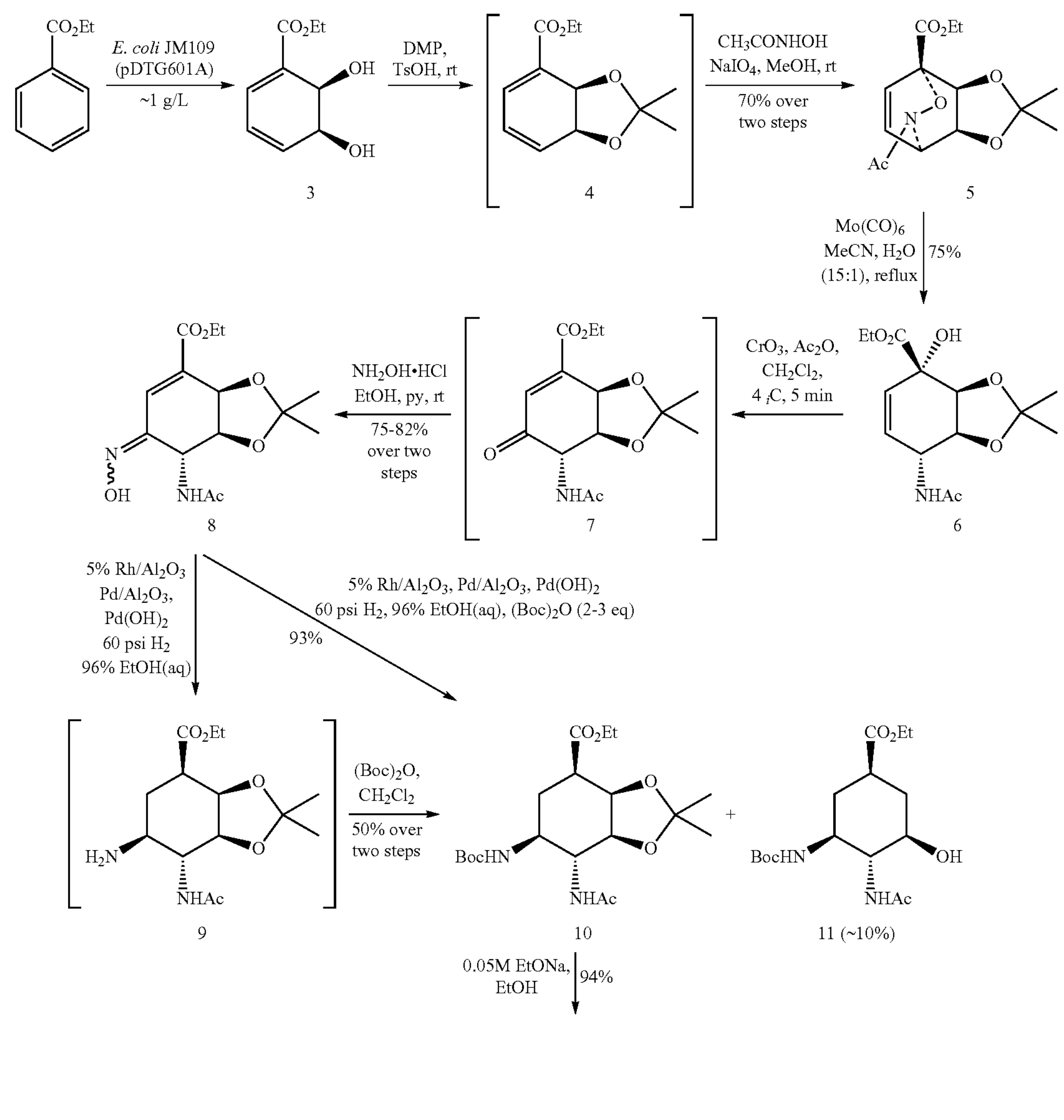

-continued

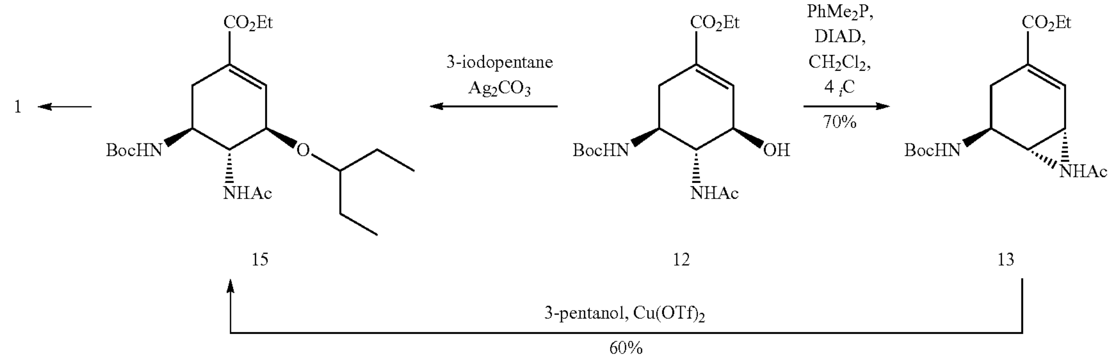

15 12 13

Example 1

(5S,6R)-ethyl 5,6-dihydroxycyclohexa-1,3-dienecarboxylate (3)—Medium-Scale Fermentation with *E. coli* JM 109(pDTG601)

(Fabris, F.; Collins, J.; Sullivan, B.; Leisch, H.; Hudlicky, T. *Org. Biomol. Chem.* 2009, 7, 2619-2627).

(a) Plate Preparation.

Agar plates consist of bactotryptone (10 g $L^{-1}$), yeast extract (5 g $L^{-1}$), NaCl (5 g $L^{-1}$), agar (15 g $L^{-1}$), and ampicillin (200 mg $L^{-1}$). Previously thawed *E. coli* JM 109 (pDTG601) 8 cells in cryovials were streaked onto a plate. The streaked plate was incubated at 35° C. for 1 d. Single-cell colonies, which have a dark tinge, were chosen for the preparation of preculture.

(b) Preculture Preparation and Inoculation.

A mineral salts broth (MSB, 600 mL) containing $K_2HPO_4$ (9.6 g), $KH_2PO_4$ (8.4 g), $(NH_4)_2SO_4$ (3 g), yeast extract (9 g), glucose (18 g), and $MgSO_4.7H_2O$ (1.2 g) was divided into two 2.8-L Fernbach flasks and sterilized. After the broth is cooled to room temperature, ampicillin (60 mg in 6 mL of autoclaved water) is added, and each flask is inoculated with a single colony of *E. coli* JM 109 (pDTG601) from a fully grown plate. These preculture flasks were placed in an orbital shaker (35° C., 150 rpm) for 12 h.

(c) Sterilization of Fermentor.

The production medium in the fermentor consisted of an aqueous solution of $KH_2PO_4$ (84.3 g), citric acid (22.5 g), $MgSO_4.7H_2O$ (22.5 g), trace metal solution [12.5 mL: $Na_2SO_4$ (1 g $L^{-1}$), $MnSO_4$ (2 g $L^{-1}$), $ZnCl_2$ (2 g $L^{-1}$), $CoCl_2.6H_2O$ (2 g $L^{-1}$), $CuSO_4.5H_2O$ (0.3 g $L^{-1}$), $FeSO_4.7H_2O$ (10 g $L^{-1}$), pH 1.0], concentrated $H_2SO_4$ (12.5 mL), and ferric ammonium citrate (3.75 g). The fermentor containing these ingredients and approximately 10 L of water was sterilized at 120° C. for 20 min. The fermentor was allowed to cool to 35° C., and air was passed through the fermentor at a flow rate of 3 L/min. The stirrer was set at 500 rpm while the pH was gradually adjusted to 6.8 by means of automatic addition of ammonium hydroxide. Once the desired pH was reached, thiamine (200 mg in 8 mL of autoclaved water) and ampicillin (500 mg in 8 mL of autoclaved water) were added to the fermentor.

(d) Transfer of Precultures to Fermentor.

On day two, the pre-cultures were transferred to the fermentor, and stirring was reduced to 300 rpm. A sample was taken from the fermentor immediately after adding the pre-cultures to serve as a blank for monitoring the increase in optical density (OD) of the fermentor medium. UV absorbance at 640 nm (1 to 100 dilution) was measured at 2 h intervals after transfer. The stirring was increased to 800 rpm and air was passed through the fermentor at a flow rate of 8 L/min. After approximately 4 h Glucose (720 g $L^{-1}$) was then introduced to the medium in 30 min intervals. During this time, the dissolved oxygen content gradually decreased until it reached a minimum and then sharply increased, which usually occurred 10 h after the addition of precultures. When the turbidity or OD of the medium had reached 15 times that of the blank as measured by UV absorbance (typically at 14 h after addition of precultures), IPTG (200 mg) is added to induce the production of toluene dioxygenase.

(e) Feeding of Substrate.

Ethylbenzoate was introduced via peristaltic pump in 2 gram increments with 15 min between each feeding cycle. A total of 24 g of ethylbenzoate was introduced into the fermentor. All parameters were kept at standard operating values for a further 20 minutes following feeding of substrate.

(f) Harvesting of Culture and Metabolite.

The pH of the medium in the fermentor was adjusted to 7.5 and cooled to 20° C. after the biotransformation. The broth is centrifuged at 7000 rpm and 5° C. for 20 min. The supernatant liquid was decanted and saved for extraction; the residue of cell material was collected and autoclaved at 120° C. for 20 min prior to disposal.

(g) Isolation of Metabolite.

The supernatant liquid was extracted three times with one-third its volume of ethyl acetate. The combined organic extracts were dried over $Na_2SO_4$, filtered, and evaporated without heating to dryness to afford the crude diol (19 g as the major component in a 3:1 mixture with recovered substrate). Crystallization from diethylether-hexane yielded diol as white solid; mp 48° C. (ethyl acetate-hexanes); $R_f$ 0.31 (1:2 hexanes-ethyl acetate); $[\alpha]^{23}_D$=+54.7 (c 3.75, $CHCl_3$); IR (film, $cm^{-1}$) ν 3385, 2981, 2934, 1700, 1280, 1243, 1104, 1068, 825, 771; $^1H$ NMR (300 MHz, $CDCl_3$) δ 7.04 (d, J=5.3 Hz, 1H), 6.15 (dt, J=1.1, 9.4 Hz, 1H), 6.03 (dq, J=2.25, 9.22 Hz, 1H), 4.49-4.55 (m, 1H), 4.40-4.48 (m, 1H), 4.22 (q, J=7.0 Hz, 2H), 3.65-3.78 (m, 2H), 1.28 (t, J=7.2 Hz, 3H); $^{13}C$ NMR (75 MHz, $CDCl_3$) δ 167.1, 138.7, 134.1, 128.7, 122.5, 69.8, 64.5, 60.9, 14.2; MS (EI) m/z (%) 184 (M), 45(20), 51(21), 77(39), 105(100), 121(52), 122(33), 138(26), 166 (20); HRMS. Calcd for $C_9H_{12}O_4$: 184.0736. Found: 184.0731; Anal. Calcd for $C_9H_{12}O_4$: C, 58.69; H, 6.57. Found: C, 58.77; H, 6.60.

Example 2

3-acetyl-1-ethoxycarbonyl-5,6-O-isopropylidine-2-oxa-3-azabicyclo[2.2.2]oct-7-ene-5,6-diol (5)

To a stirred solution of diol 3 (5 g, 27.1 mmol) in 2,2-dimethoxypropane (80 mL) was added p-toluenesulfonic acid (catalytic amount) at room temperature. After complete consumption of starting material (TLC analysis), the solution was cooled to 0° C. before the addition of $H_2O$ (10 mL). On a preparative scale the intermediate acetonide (3aR,7aS)-ethyl 2,2-dimethyl-3a,7a-dihydrobenzo[d][1,3]dioxole-4-carboxylate (4) was not isolated but taken directly to the next step. Analytical samples were purified by flash column chromatography [hexanes-ethyl acetate (9:1)]. Data for the protected diol 4: $R_f$ 0.3 (9:1, hexanes-ethyl acetate); $[\alpha]^{23}_D$=+50.71 (c 0.89, $CHCl_3$); IR (film, $cm^{-1}$) ν 3433, 2985, 1730, 1646, 1370, 1260, 1163, 1072, 1026.8; $^1$H NMR (300 MHz, $CDCl_3$) δ 7.1-7.11 (m, 1H), 6.06-6.07 (m, 2H), 4.82-4.92 (m, 2H), 4.20-4.29 (m, 2H), 1.42 (s, 3H), 1.35 (s, 3H), 1.29 (t, J=7.2 Hz, 3H); $^{13}$C NMR (75 MHz, $CDCl_3$) δ 166.1, 133.8, 133.6, 126.3, 121.3, 105.5, 72.5, 68.1, 60.8, 26.7, 25.0, 14.2; MS (EI) m/z (%): 209 ($M^+$−$CH_3$), 167 (33), 166 (40), 139 (41), 121 (92), 95 (85), 43 (100); HRMS. Calcd for $C_{12}H_{16}O_4$: 224.10486. Found: 224.10450. $NaIO_4$ (5.80 g, 27.1 mmol) was added to the reaction mixture above prior to the dropwise addition of a solution of acetohydroxamic acid (2.03 g, 27.1 mmol) in MeOH (25 mL) over 5 minutes. The resulting solution was stirred at room temperature for 16 h then diluted with ethyl acetate (300 mL). Inorganic precipitate was filtered off and resulting solution was washed with saturated solution of $NaHCO_3$(2×20 mL). Organic layer was dried over $Mg_2SO_4$ and evaporated. The crude material was purified via flash column chromatography [hexane-ethyl acetate (1:4)] to yield oxazine 5 (5.65 g, 70% over 2 steps) as a white solid; mp 89-90° C. (hexanes-ethyl acetate): $R_f$ 0.33 (3:7 hexane-ethyl acetate); $[\alpha]^{23}_D$=−18.0 (c 0.54, $CHCl_3$); IR (film, $cm^{-1}$) ν 3466, 2938, 2987, 1747, 1684, 1620, 1372, 1275, 1086; $^1$H NMR (600 MHz, $CDCl_3$) δ 6.57-6.65 (m, 2H), 5.47-5.52 (m, 1H), 4.71 (d, J=6.8 Hz, 1H), 4.56 (dd, J=4.7, 6.6 Hz, 1H), 4.38 (q, J=7.2 Hz, 2H), 2.01 (s, 3H), 1.38 (t, J=7.2 Hz, 3H), 1.32 (s, 3H), 1.30 (s, 3H); $^{13}$C NMR (150 MHz, $CDCl_3$) δ 173.9, 166.6, 132.4, 128.4, 111.7, 79.2, 76.1, 72.8, 62.7, 50.0, 25.6, 25.4, 21.7, 14.1; MS (EI) m/z (%): 297 ($M^+$), 124(52), 105(35), 100(32), 96(30), 43 (100); HRMS. Calcd for $C_{14}H_{19}NO_6$: 297.1212. Found: 297.1215.

Example 3

(3aS,4S,7R,7aS)-ethyl 7-acetamido-4-hydroxy-2,2-dimethyl-3a,4,7,7a-tetrahydrobenzo[d][1,3]dioxole-4-carboxylate (6)

To a stirred solution of oxazine 5 (955 mg, 3.21 mmol) in 15:1/$CH_3CN$:$H_2O$ (10 mL) was added molybdenum hexacarbonyl (848 mg, 3.21 mmol) at room temperature. After 3 h stirring at 85° C. the reaction mixture was diluted with dichloromethane (50 mL) filtered through a plug of celite and evaporated. The crude material was purified via flash column chromatography [hexane-ethyl acetate (9:1)→ethyl acetate] to yield alcohol 6 (720 mg, 75%) as a white solid; mp 97-99° C. (hexanes-ethyl acetate); $R_f$ 0.20 (ethyl acetate); $[\alpha]^{23}_D$=−94.3 (c=0.79, $CHCl_3$); IR (film, $cm^{-1}$) ν 3433, 2094, 1644, 1271, 1217, 1060; $^1$H NMR (600 MHz, $CDCl_3$) δ 6.25 (d, J=8.7 Hz, 1H), 5.98 (dd, J=3.8, 9.8 Hz, 1H), 5.94 (dd, J=0.9, 9.9 Hz, 1H), 4.77-4.81 (m, 1H), 4.37 (t, J=8.3 Hz, 1H), 4.34 (dd, J=4.3, 7.7 Hz, 1H), 4.22-4.29 (m, 2H), 4.12 (s, 1H), 1.99 (s, 3H), 1.35 (s, 3H), 1.32 (t, J=7.4 Hz, 3H), 1.28 (s, 3H); $^{13}$C NMR (150 MHz, $CDCl_3$) δ 172.7, 170.0, 132.9, 129.6, 109.3, 81.0, 76.3, 74.5, 62.8, 48.8, 26.2, 24.2, 23.5, 14.0; MS (EI) m/z (%): 284 ($M^+$−$CH_3$), 199(99), 153(38), 125(36), 96(37), 86(61), 84(100), 83(47), 43 (90); HRMS. Calcd for $C_{13}H_{18}NO_6$: 284.1130. Found: 284.1137.

Example 4

(3aR,7R,7aS)-ethyl-7-acetamido-6-(hydroxyimino)-2,2-dimethyl-3a,6,7,7a-tetrahydrobenzo[d][1,3]dioxole-4-carboxylate (8)

The oxidizing agent was prepared by stirring $CrO_3$ (835 mg; 8.35 mmol) in $Ac_2O$ (2 mL) at 80° C. After 7 min the resulting slurry was allowed to cool to room temperature diluted with 6 ml of DCM and cooled in ice-bath. This solution was added over 30 sec to a cooled (4° C.) solution of tertiary alcohol 6 (1 g; 3.34 mmol) in DCM (20 mL). After 5 min of stirring the reaction was quenched by addition of 8 mL EtOH, pyridine (0.4 mL) and solid $NaHCO_3$ (2 g). Reaction mixture was then stirred additional 5 min in ice bath and 30 min at room temperature. On a preparative scale the intermediate enone (3aR,7S,7aS)-ethyl-7-acetamido-2,2-dimethyl-6-oxo-3a,6,7,7a-tetrahydrobenzo[d][1,3]dioxole-4-carboxylate (7) was not isolated and taken directly to the next step. Analytical sample was purified via flash column chromatography (ethyl acetate) Analytical data for intermediary enone 7: Colorless oil: $R_f$ 0.6 (ethyl acetate); $[\alpha]^{20}_D$=+19.35 (c=1, $CHCl_3$); IR (KBr, $cm^{-1}$) ν 3385, 2988, 1724, 1712, 1662, 1543, 1383, 1253, 1077, 1024; $^1$H NMR (300 MHz, $CDCl_3$) δ 6.94 (s, 1H), 6.10 (d, J=5.4 Hz, 1H), 5.13 (d, J=4.8 Hz, 1H), 4.82 (m, 1H), 4.39 (m, 1H), 4.35 (q, J=7.2 Hz, 1H), 2.10 (s, 3H), 1.61 (s, 3H), 1.48 (s, 3H), 1.36 (t, J=7.2 Hz, 3H); $^{13}$C (75 MHz, $CDCl_3$) δ 195.0, 170.8, 164.5, 140.7, 134.5, 112.0, 70.3, 62.3, 58.3, 27.7, 26.4, 23.2, 14.0; MS (EI) m/z (%): 297 ($M^+$), 239 (4), 221 (4), 197 (14), 175 (13), 151 (11), 84 (100), 43 (34); HRMS. Calcd for $C_{14}H_{19}NO_6$: 297.1212. Found: 297.1218.

The above reaction mixture was again cooled in ice-bath and $NH_2OH.HCl$ (2.32 g; 33.43 mmol) was added at once. After 1 h of stirring in ice-bath the reaction mixture was allowed to warm to room temperature and stirred additional 16 h. The mixture was then diluted with ethyl acetate (130 mL) and extracted 4×8 mL with saturated $NaHCO_3$ solution. Combined aqueous layers were re-extracted with ethyl acetate (30 ml). Combined organic layer was dried with $MgSO_4$ and evaporated. Chromatography of residue [hexane-ethyl acetate (1:1)→ethyl acetate, 30 g silica] afforded 860 mg (82%) of oxime 8 as slightly green oil. Product was crystallized from 2-propanol-hexane as white solid; m.p. 106-116° C.; $R_f$ 0.30 (ethyl acetate); $[\alpha]^{20}_D$=−52.63 (c=1, $CHCl_3$); IR (KBr, $cm^{-1}$) ν 3367, 2988, 1720, 1659, 1547, 1382, 1246, 1069, 1023; $^1$H NMR (300 MHz, $CDCl_3$) δ 9.65 (bs, 1H), 7.77 (s, 1H), 6.29 (d, J=8.4 Hz, 1H), 5.04 (d, J=5.4 Hz, 1H), 5.02 (dd, J=8.4, 8.1 Hz, 1H), 4.32 (m, 1H), 4.30 (m, 2H), 2.06 (s, 3H), 1.49 (s, 3H), 1.44 (s, 3H), 1.36 (t, J=7.2 Hz, 3H); $^{13}$C (75 MHz, $CDCl_3$) δ 171.2, 165.4, 148.9, 132.4, 124.8, 111.1, 76.0, 70.6, 61.7, 49.9, 27.9, 26.4, 23.3, 14.1; MS (FAB+) m/z (%) 313 $(M+H)^+$, 255(73), 195(76), 150(16), 43 (38); HRMS. Calcd for $C_{14}H_{21}N_2O_6$: 313.13996. found 313.14056; Anal. Calcd for $C_{14}H_{21}N_2O_6$: C, 53.84; H, 6.45. Found: C, 54.80; H, 7.52, crystals contain 15 mol. % of 2-propanol.

Example 5

(3aR,6S,7R,7aS)-7-Acetylamino-6-tert-butoxycarbonylamino-2,2-dimethyl-3a,6,7,7a-tetrahydro-benzo[1,3]dioxole-4-carboxylic acid ethyl ester (10)

Procedure A ("Stepwise"):

Suspension of oxime 8 (400 mg; 1.27 mmol) and 100 mg $Rh/Al_2O_3$ (5%) in EtOH (96%, 45 mL) was hydrogenated in the Parr apparatus (60 pound/inch$^2$). After 16 h the reaction mixture was filtered through short bed of celite and evaporated. On a preparative scale the amine (3aR,4R,6S,7R,7aS)-ethyl-7-acetamido-6-amino-2,2-dimethylhexa-hydrobenzo[d][1,3]dioxole-4-carboxylate (9) was not isolated but taken directly to the next step. Analytical sample was purified via flash column chromatography [dichloromethane-methanol (1:1)] to yield amine 9 as colorless oil: $R_f$ 0.26 (1:1 dichloromethane-methanol); $[\alpha]^{20}_D$=−11.54 (c=1, $CHCl_3$); IR (KBr, cm$^{-1}$) ν 3445, 2984, 1733, 1654, 1556, 1384, 1222, 1144, 1049; $^1$H NMR (600 MHz, $CDCl_3$) δ 5.52 (d, J=8.4 Hz, 1H), 4.58 (dd, J=4.8, 4.2 Hz, 1H), 4.28 (m, 1H), 4.19 (m, 1H), 4.05 (dd, J=8.4, 4.8 Hz, 1H), 3.56 (dd, J=10.8, 8.4 Hz, 1H), 2.81 (ddd, J=13.2, 4.2, 4.2 Hz, 1H), 2.76 (m, 1H), 2.06 (s, 3H), 2.04 (m, 1H), 1.85 (ddd, J=13.2, 11.9, 11.9 Hz, 1H), 1.55 (s, 3H), 1.36 (s, 3H), 1.28 (t, J=7.2, 3H); $^{13}$C (75 MHz, $CDCl_3$) δ 171.1, 170.8, 109.7, 77.9, 74.0, 60.9, 59.7, 50.8, 41.4, 30.9, 28.1, 26.2, 23.8, 14.1; MS (FAB) m/z (%): 301 (M$^+$+H), 273 (8), 226 (7), 184 (13), 151 (7), 110 (9), 43 (13); HRMS. Calcd for $C_{14}H_{24}N_2O_5$: 300.1685. Found: 300.1800.

The crude product above was dissolved in dichloromethane (DCM) (20 ml) and $Boc_2O$ (800 mg; 3.66 mmol) was added and the mixture stirred at room temperature. The progress of the reaction was monitored by TLC (ethyl acetate-hexane 1:1). After 6 hours the reaction mixture was diluted with DCM (45 ml) and washed with saturated solution of $NaHCO_3$(5 mL+1 g of solid $NaHCO_3$). Organic layer was dried with $MgSO_4$ and evaporated. Chromatography of residue [ethyl acetate-hexane (3:1)→ethyl acetate, 15 g silica] afforded 260 mg (50%) of protected amide 10 as white solid and ~10% of over-hydrogenated byproduct (1R,3S,4R,5R)-ethyl 4-acetamido-3-(tert-butoxycarbonylamino)-5-hydroxycyclohexanecarboxylate (11).

Analytical data for major product 10: White solid: m.p.=174-175° C. (ethyl acetate-hexane); $R_f$=0.3 (ethyl acetate); $[\alpha]^{20}_D$=−33.51 (c=1, $CHCl_3$); IR (KBr, cm$^{-1}$) ν 3349, 2978, 2930, 2885, 2360, 2340, 1731, 1682, 1656, 1528, 1459.87, 1384, 1371, 1346, 1289, 1253, 1219, 1166, 1120, 1092, 1064, 1044, 1024, 1008, 988, 969, 958, 929, 905, 870, 800, 781, 755, 715, 696, 653, 624, 586, 545, 514, 464, 431; $^1$H NMR ($CDCl_3$, 600 MHz) δ 5.63 (d, J=9.3 Hz, 1H), 4.96 (d, J=8.7 Hz, 1H), 4.57 (dd, 2×J=3.9, 3.9 Hz, 1H), 4.33-4.18 (m, 2H), 4.00 (ddd, J=11.4, 9.3, 9.0 Hz, 1H), 3.86 (dd, J=4.5, 9.0 Hz, 1H), 3.38 (m, 1H), 2.83 (ddd, J=4.2, 4.2, 8.7 Hz, 1H), 2.12 (ddd, J=3.9, 3.9, 9.6 Hz, 1H), 2.01 (s, 3H), 1.92 (ddd, J=13.2, 13.2, 13.2 Hz, 1H), 1.43 (s, 9H), 1.36 (s, 3H), 1.28 (s, 3H), 1.27 (t, J=7.2 Hz, 3H); $^{13}$C NMR ($CDCl_3$, 150 MHz) δ 171.27, 170.40, 109.93, 79.73, 78.66, 73.76, 61.03, 55.22, 50.78, 41.38, 29.71, 28.33, 27.99, 26.23, 23.43, 14.16; MS (EI+) m/z (%): (M$^+$−$CH_3$) 385(3), 341(11), 329(15), 311 (20); HRMS. Calcd for $C_{18}H_{29}N_2O_7$: 385.19748. Found: 385.19829; Anal. Calcd for $C_{19}H_{32}N_2O_7$: C, 56.99; H, 8.05; N, 7.00. Found C, 57.13; H, 8.19; N, 6.93.

Analytical data for minor product 11: Gelly solid; m.p.=180° C. (ethyl acetate-hexane); $R_F$=0.1 (ethyl acetate); $[\alpha]^{20}_D$=−90.0 (c=1, $CHCl_3$); IR (KBr, cm$^{-1}$) ν 3357, 2979, 2936, 2871, 1725, 1686, 1654, 1569, 1559, 1526, 1457, 1384, 1340, 1328, 1317, 1284, 1244, 1171, 1129, 1079, 1023, 999; $^1$H NMR ($CDCl_3$, 600 MHz) δ 6.91 (bs, 1H), 5.01 (d, J=7.2 Hz, 1H), 4.16-4.11 (m, 2H), 3.55 (m, 2H), 3.48 (m, 1H), 2.44 (dddd, 1H, J=12.0, 12.0, 3.6, 3.6 Hz, 1H), 2.34 (m, 1H), 2.18 (m, 1H), 2.00 (s, 3H), 1.56-1.50 (m, 2H), 1.49 (s, 9H), 1.45 (t, J=7.2 Hz, 3H); $^{13}$C NMR ($CDCl_3$, 150 MHz) δ 173.64, 173.46, 80.38, 73.35, 62.01, 60.88, 50.61, 38.70, 36.16, 33.58, 28.26, 23.15, 14.14; MS (FAB+) m/z (%): 345 (M$^+$+H), 289(45), 245(100), 168 (26); HRMS. Calcd for $C_{16}H_{29}N_2O_6$: 345.20525. Found 345.20256; Anal. Calcd for $C_{16}H_{28}N_2O_6$: C, 55.80; H, 8.19; N, 8.13. Found C, 55.25; H, 8.24; N, 7.56. Procedure B ("one-pot")

Suspension of oxime 8 (73 mg; 0.24 mmol), $Boc_2O$ (0.105 mg; 0.48 mmol) and 20 mg $Rh/Al_2O_3$ (5%) in EtOH (96%, 2 mL) was hydrogenated in Parr apparatus (60 pound/inch$^2$). After 16 h the reaction mixture was filtered through a short bed of celite and concentrated. Chromatography [ethyl acetate, 6 ml silica] yield 87 mg (93%) of amide 10 as white solid.

Example 6

(3R,4R,5S)-4-Acetylamino-5-tert-butoxycarbonylamino-3-hydroxy-cyclohex-1-enecarboxylic acid ethyl ester (12)

Acetonide 10 (534 mg; 1.33 mmol) was dissolved in EtOH (10 mL) and 12.4 ml of ethanolic sodium ethoxide solution (0.05M) was added dropwise over period 1 min. After 5 min of stirring at room temperature reaction mixture was quenched by addition of 1 g of silica and then filtered and evaporated. Chromatography [ethyl acetate→ethyl acetate-ethanol (1:1), 5 g silica] of residue afforded 432 mg (94%) of allylalcohol 12 as white solid: m.p.=177-178° C. (ethyl acetate-hexane); $R_f$=0.2 (ethyl acetate); $[\alpha]^{20}_D$=−9.14 (c=1, $CHCl_3$); IR (KBr, cm$^{-1}$) ν 3341, 2926, 2854, 2360, 2326, 1726, 1680, 1654, 1626, 1530, 1460, 1319, 1295, 1249, 1165, 1127, 1091, 1046, 1025, 992, 946, 908, 863, 782, 755, 735, 644, 607, 590, 571, 543, 491, 460, 437; $^1$H NMR ($CDCl_3$, 600 Mhz) δ 7.35 (d, J=5.8 Hz, 1H), 6.83 (dd, J=2.4, 2.4 Hz, 1H), 5.07 (bs, 1H), 4.92 (d, J=7.9 Hz, 1H), 4.36-4.29 (m, 1H), 4.27-4.16 (m, 2H), 3.85-3.83 (m, 1H), 3.77-3.73 (m, 1H), 2.84 (dd, 1H, J=17.4, 5.1 Hz, 1H), 2.21 (dddd, J=17.4, 11.0, 2 x≈3 Hz, 1H), 2.03 (s, 3H), 1.47 (s, 9H), 1.30 (t, J=7.2 Hz, 3H); $^{13}$C NMR ($CDCl_3$, 150 Mhz) δ 173.61, 165.86, 157.64, 139.05, 127.65, 80.87, 73.60, 61.05, 60.55, 48.05, 30.83, 28.23, 23.09, 14.17; MS (FAB+) m/z %: 343 (M$^+$+H), 287 (100), 243(25), 208 (30); HRMS. Calcd for $C_{16}H_{27}N_2O_6$: 343.18691. Found: 343.18417; Anal. Calcd for $C_{16}H_{27}N_2O_6$: C, 56.13; H, 7.65; N, 8.18. Found C, 56.31; H, 7.83; N, 8.17.

Example 7

(1S,5S,6R)-ethyl 7-acetyl-5-(tert-butoxycarbonylamino)-7-azabicyclo[4.1.0]hept-2-ene-3-carboxylate (13)

To a cooled (4° C.) solution of $PhMe_2P$ (71 mg; 0.52 mmol) in dichloromethane (1 mL) was added dropwise during 1 min DIAD (104 mg; 0.52 mmol). After additional 5 min of stirring a solution of alcohol 12 (84 mg; 0.24 mmol) and $Et_3N$ (7 μL; 0.05 mmol) in dichloromethane (1 mL) was added dropwise. After 10 min the reaction mixture was directly loaded on a silica column. Chromatography [hexane-ethyl acetate (3:1)→(2:1), 6 ml silica] afforded 53 mg (70%) of aziridine 13 as a colourless oil with trace amounts of 14.

$R_f$=0.7 (ethyl acetate-hexane 1:1); $[\alpha]^{20}_D$=−81.47 (c=1, $CHCl_3$); IR (KBr, $cm^{-1}$) ν 3352, 2980, 2933, 2876, 1708, 1645, 1525, 1455, 1384, 1386, 1263, 1196, 1170, 1097, 1048, 1024, 756; $^1H$ NMR ($CDCl_3$, 600 Mhz) δ 7.21 (dd, J=4.2, 3.0 Hz, 1H), 4.57 (m, 1H), 4.48 (d, J=7.8 Hz, 1H), 4.22 (m, 2H), 3.15 (m, 1H), 3.13 (m, 1H) 2.75 (d, J=17.4 Hz, 1H), 2.34 (m, 1H), 2.16 (s, 3H), 1.45 (s, 9H), 1.30 (t, J=7.2 Hz, 3H); $^{13}C$ NMR ($CDCl_3$, 150 Mhz) δ 181.34, 165.89, 155.04, 133.77, 130.29, 80.10, 61.11, 42.00, 41.05, 31.90, 28.34, 28.29, 26.70, 23.18, 14.20; MS (EI+) m/z %: 324 ($M^+$), 268(8), 251(6), 222(19), 207(45), 165 (80); HRMS. Calcd for $C_{16}H_{24}N_2O_5$: 324.16781. Found: 324.16852.

(3aR,4S,7aS)-ethyl 4-(tert-butoxycarbonylamino)-2-methyl-3a,4,5,7a-tetrahydrobenzo[d]oxazole-6-carboxylate (14)

m.p.=45-49° C. (ethyl ether-hexane); $R_f$=0.3 (ethyl acetate-hexane 1:1); $[\alpha]^{20}_D$=+29.38 (c=1, $CHCl_3$); IR (KBr, $cm^{-1}$) ν 3385, 2978, 2929, 2854, 1718, 1669, 1529, 1455, 1384, 1368, 1298, 1251, 1226, 1171, 993; $^1H$ NMR ($CDCl_3$, 300 Mhz) δ 6.94 (dd, J=1.5, 1.8 Hz, 1H), 5.00 (dd, J=2.4, 9.0 Hz, 1H), 4.82 (d, J=5.7 Hz, 1H), 4.22 (m, 2H), 4.14 (ddd, J=1.2, 8.4, 9.0 Hz, 1H), 3.68 (m, 1H), 2.90 (dd, J=3.0, 17.4, 1H), 2.21 (m, 1H), 2.16 (d, J=1.2 Hz, 3H), 1.45 (s, 9H), 1.32 (t, J=7.2 Hz, 3H); $^{13}C$ NMR (DMSO-80° C., 75 Mhz) δ 165.98, 164.32, 155.59, 133.14, 132.65, 78.39, 75.15, 66.97, 60.98, 50.56, 28.75, 27.82, 14.40, 14.02; MS (FAB+) m/z %: 325 ($M^+$+H), 269(63), 243(19), 149 (49); HRMS. Calcd for $C_{16}H_{25}N_2O_5$: 325.17748. Found: 325.17635.

Example 8

(3R,4R,5S)-ethyl 4-acetamido-5-(tert-butoxycarbonylamino)-3-(pentan-3-yloxy)cyclohex-1-enecarboxylate (15)

To a solution of aziridine 13 (16 mg; 0.05 mmol) in 3-pentanol (1 mL) was added $Cu(OTf)_2$ (3 mg; 0.008 mmol). After 16 h the reaction mixture was quenched by addition of saturated solution of $NaHCO_3$ (0.1 ml) and concentrated. Chromatography of residue [hexane-ethyl acetate (3:1)→(2:1), 4.5 ml silica] afforded 12 mg (60%) of compound 15 as white solid: m.p.=144-145° C. ($CHCl_3$); $R_F$=0.3 (ethyl acetate-hexane 1:2); $[\alpha]^{20}_D$=−21.54 (c=0.5, $CHCl_3$); IR (KBr, $cm^{-1}$) ν 3324, 2976, 3966, 2933, 2877, 2855, 1720, 1687, 1658, 1587, 1536, 1459, 1384, 1297, 1250, 1176, 1146, 1130, 1086, 1054, 1019, 948; $^1H$ NMR ($CDCl_3$, 600 Mhz) δ 6.81 (s, 1H), 5.80 (d, J=9.6 Hz, 1H), 5.11 (d, J=9.0 Hz, 1H), 4.22 (m, 2H), 4.08 (ddd, J=2 x≈4.8, 9.3 Hz, 1H), 3.97 (m, 1H), 3.81 (ddd, J=5.1, 2×9.6 Hz, 1H), 3.37 (qui, J=5.7 Hz, 1H), 2.76 (dd, J=4.8, 17.7 Hz, 1H), 2.31 (m, 1H), 2.00 (s, 3H), 1.51 (m, 4H), 1.44 (s, 9H), 1.30 (t, J=7.2 Hz, 3H), 0.90 (m, 6H); $^{13}C$ NMR ($CDCl_3$, 150 Mhz) δ 170.85, 165.98, 156.35, 137.65, 129.34, 82.21, 79.73, 76.00, 61.00, 54.47, 49.00, 31.01, 28.33, 26.12, 25.69, 23.41, 14.20, 9.54, 9.21.

Example 9

Sodium (3aS,4S,7R,7aS)-7-acetamido-4-hydroxy-2,2-dimethyl-3a,4,7,7a-tetrahydrobenzo[d][1,3]dioxole-4-carboxylate (16)

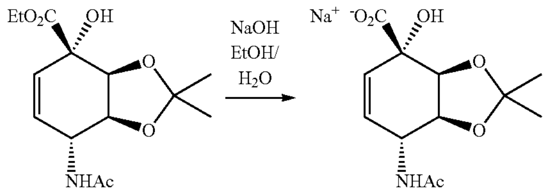

6 16

To a stirred solution of ester 6 (55 mg, 0.185 mmol) in $EtOH/H_2O$ (4/1, 1.5 mL) were added 3 drops of 1M NaOH. The pH of the reaction mixture was checked and maintained at basic level by addition of 3 more drops of NaOH in 2 h. When TLC (EtOAc) did not show any starting material, a spatula tip of silicagel was added to the mixture and the mixture was stirred at r.t. until the pH of the mixture became neutral. The mixture was then filtered and solvents evaporated. The crude material was purified by column chromatography (5 mL of silicagel) with a solvent system DCM/MeOH 6/1→4/1, which gave the product as a yellowish glassy compound (48 mg, 86%).

$R_F$=0.15 (DCM/MeOH 4/1); $[\alpha]_D^{20}$=−127.777 (c 1, MeOH); IR (KBr) ν 3373, 2988, 2926, 1726, 1656, 1553, 1383, 1269, 1213, 1117, 1074, 876, 752, 710 $cm^{-1}$; $^1H$ NMR (300 MHz, MeOD) δ 5.81 (dd, 1H, J=1.2, 10.5 Hz), 5.75 (dd, 1H, J=2.1, 10.2 Hz), 4.87 (t, 1H, J=2.1 Hz), 4.34-4.27 (m, 2H), 2.00 (s, 3H), 1.42 (s, 3H), 1.33 (s, 3H) ppm; $^{13}C$ NMR (75 MHz, MeOD) δ 171.4, 131.4, 130.8, 108.9, 81.0, 76.5, 50.5, 25.3, 23.3, 21.5 ppm; MS (FAB+) m/z %: 316 (M+$Na^+$) (58), 294 (M+$H^+$) (100), 272 (M−$Na^+$+$2H^+$) (27), 214 (34), 176 (32), 149 (13), 109 (14), 81 (17), 69 (17), 55 (26), 43 (41); HRMS Calc'd for $C_{12}H_{18}NO_6$: 272.11341 found: 272.11170.

Example 10

Sodium (3aR,7R,7aS,E)-7-acetamido-6-(hydroxyimino)-2,2-dimethyl-3a,6,7,7a-tetrahydrobenzo[d][1,3]dioxole-4-carboxylate (17)

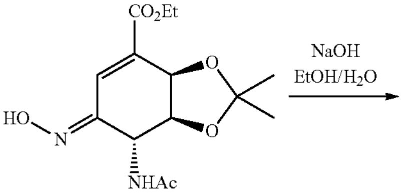

8

-continued

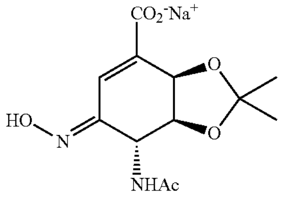

17

To a stirred solution of ester 8 (53 mg, 0.170 mmol) in $EtOH/H_2O$ (4/1, 2 mL), 4 drops of 1M NaOH were added at r.t. After 2 h only starting material was present, so the mixture is heated at 55° C. for next 4 h, during which 6 more drops of 2M NaOH were added. When TLC (EtOAc) did not show any starting material, a spatula of silicagel was added to the mixture and the mixture was stirred at r.t. until neutral pH. The mixture was then filtered and solvents evaporated. The crude material was purified by column chromatography (5 mL of silicagel) with a solvent system DCM/MeOH 2/1 to give the product as a yellowish glassy compound (39 mg, 75%).

$R_F$=0.2 (DCM/MeOH 2/1); $[\alpha]_D^{20}$=−1.195 (c 1, MeOH); IR (KBr) ν 3352, 3267, 3065, 2991, 2937, 1707, 1660, 1552, 1383, 1226, 1066, 967, 864, 734 $cm^{-1}$; $^1H$ NMR (300 MHz, MeOD) δ 7.72 (s, 1H), 5.05 (d, 1H, J=5.4 Hz), 4.88 (d, 1H, J=6.3 Hz), 4.38 (t, 1H, J=5.7 Hz), 1.99 (s, 3H), 1.40 (s, 3H), 1.38 (s, 3H) ppm; $^{13}C$ NMR (75 MHz, MeOD) δ 172.0, 147.9, 122.9, 110.0, 75.4, 70.8, 49.4, 26.9, 25.3, 21.2 ppm; MS (FAB+) m/z %: 329 ($M+Na^+$) (31), 285 ($M-Na^++2H^+$) (84), 227 (54), 176 (100), 167 (45), 84 (12), 59 (13), 43 (49); HRMS Calc'd for $C_{12}H_{17}N_2O_6$: 285.10866 found: 285.10902.

Example 11

Sodium (3aR,6R,7R,7aS)-7-acetamido-6-hydroxy-2,2-dimethyl-3a,6,7,7a-tetrahydrobenzo[d][1,3]dioxole-4-carboxylate (19)

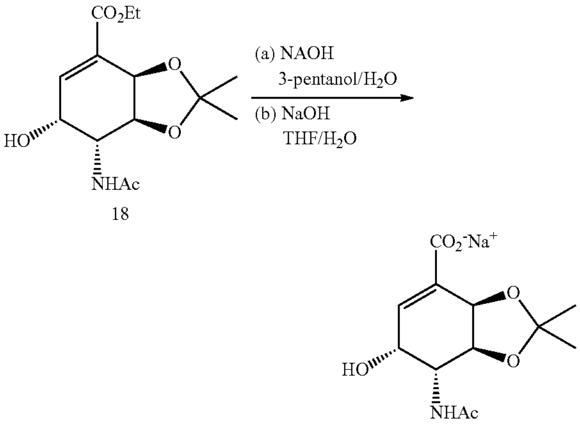

18

19

To a stirred solution of a) ester 18 (13 mg, 0.043 mmol) in 3-pentanol/$H_2O$ (4/1, 1 mL)

b) ester 18 (14 mg, 0.047 mmol) in THF/$H_2O$ (4/1, 1 mL)

6 drops of 2M NaOH were added. Because TLC (EtOAc) did not show any starting material after 4 h, a spatula of silicagel was added to the mixture until neutral pH. Then the solvents were evaporated and the crude material was purified by column chromatography (5 mL of silicagel) with a solvent system DCM/MeOH 6/1→3/2 to give the product (a) 9 mg, 71%, b) 9 mg, 66%).

$R_F$=0.15 (DCM/MeOH 3/1); $[\alpha]_D^{20}$=−57.471 (c 0.5, MeOH); IR (KBr) ν 3419, 2929, 1691, 1595, 1552, 1384, 1240, 1214, 1045, 869 $cm^{-1}$; $^1H$ NMR (300 MHz, MeOD) δ 8.00 (d, 1H, J=7.5 Hz), 6.97 (d, 1H, J=3.9 Hz), 5.01 (d, 1H, J=5.4 Hz), 4.44 (t, 1H, J=3.9 Hz), 4.42-4.31 (m, 2H), 2.01 (s, 3H), 1.39 (s, 1H) ppm; $^{13}C$ NMR (75 MHz, MeOD) δ 172.7, 109.1, 73.8, 70.5, 64.0, 51.8, 26.6, 24.7, 21.2 ppm; MS (FAB+) m/z %: 294 (M+H) (8), 272 ($M-Na^++2H^+$) (100), 214 (85), 176 (17), 126 (12), 84 (7), 60 (10), 43 (26); HRMS Calc'd for $C_{12}H_{18}NO_6$: 272.11341 found: 272.11381.

Example 12

Inhibitory Potency of Compounds of the Application on Lipopolysaccharide (LPS)-Induced Neu1 Sialidase Activity in Live Raw-Blue Macrophage Cells Compounds of the application were assessed for antiviral activity using an assay that detects sialidase activity on the surface of viable cells. TOLL-like receptor-4 (TLR-4) ligand LPS induced Neu1 sialidase activity on the cell surface of live RAW-blue macrophage cells in culture after 1-2 minutes. This activity is revealed by a fluorescence (λem 450 nm) surrounding the cells treated with the fluorogenic sialidase substrate, 4MU-NeuAc (2'-(4-methylumbelliferyl)-α-N-acetylneuraminic acid) and caused by the emission of 4-methylumbelliferone. Fluorescent images were taken at 1-2 minutes after adding the substrate using epi-fluorescent microscopy (40× objective). The mean fluorescence surrounding the cells for each of the images was measured using Image J software. The sialidase activity as revealed by fluorescence (λem 450 nm) surrounding the cells was variable to nearly totally diffused for RAW-blue cells treated with LPS. The diffuse fluorescence associated with TLR ligand LPS-treated cells was due to an activation of a cellular sialidase on the cell surface and not due to a form of secreted or shed sialidase from the cells. Oseltamivir phosphate (Tamiflu®) and certail compounds of the application completely inhibited LPS=induced sialidase activity in RAW-blue macrophage cells in a dose dependent manner. The 50% inhibitory concentration ($IC_{50}$) was determined by plotting the decrease in sialidase activity against the log of the agent concentration. The results are provided in Table 1.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

| Compound | $IC_{50}$ (μM) |
|---|---|
| oseltamivir phosphate 1a (Tamiflu ®) | 0.02 |
| 16 | 0.14 |
| 17 | 0.0127 |
| 19 | 7.41 |

We claim:

1. A compound of the formula III:

III

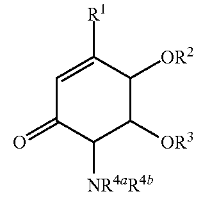

wherein $R^1$ is $CO_2Et$ or a functional group that can be converted to $CO_2Et$ selected from aryl esters, heteroaryl esters, lower alkyl esters, higher alkyl esters, thio esters, allyl esters, propargyl esters, C(O)H, C(O)OH, $C(O)O^-$, $CCl_3$, CN, C≡CH, $CH_2C$≡CH, $CH_2OH$ and alkyl ethers thereof, vinyl, $C(O\text{-alkyl})_3$, amides, alkyl amides, aryl amides, heteroaryl amides, thioesters and heterocycles;

$R^2$ and $R^3$ are independently selected from H and a suitable protecting group, or $R^2$ and $R^3$ are joined to form a suitable protecting group; and $R^{4a}$ and $R^{4b}$ are independently selected from H and a suitable protecting group or $R^{4a}$ and $R^{4b}$ are joined to form a suitable protecting group;

wherein, one or more available hydrogens in $R^1$, $R^2$, $R^3$, $R^{4a}$ and/or $R^{4b}$ is/are optionally replaced with F and/or one or more of available atoms is/are optionally replaced with an isotopic label, or a salt and/or solvate thereof.

2. A compound of the formula IV:

IV

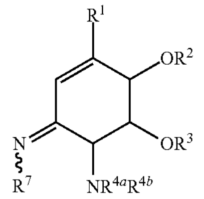

wherein $R^1$ is $CO_2Et$ or a functional group that can be converted to $CO_2Et$ selected from aryl esters, heteroaryl esters, lower alkyl esters, higher alkyl esters, thio esters, allyl esters, propargyl esters, C(O)H, C(O)OH, $C(O)O^-$, $CCl_3$, CN, C≡CH, $CH_2C$≡CH, $CH_2OH$ and alkyl ethers thereof, vinyl, $C(O\text{-alkyl})_3$, amides, alkyl amides, aryl amides, heteroaryl amides, thioesters and heterocycles;

$R^2$ and $R^3$ are independently selected from H and a suitable protecting group, or $R^2$ and $R^3$ are joined to form a suitable protecting group;

$R^{4a}$ and $R^{4b}$ are independently selected from H and a suitable protecting group or $R^{4a}$ and $R^{4b}$ are joined to form a suitable protecting group; and $R^7$ is a group that is removed under reduction or hydrogenation reaction conditions or $R^7$ is a suitable acid labile protecting group, wherein, one or more available hydrogens in $R^1$, $R^2$, $R^3$, $R^{4a}$, $R^{4b}$ and/or $R^7$ is/are optionally replaced with F and/or one or more of available atoms is/are optionally replaced with an isotopic label, or a salt, solvate and/or prodrug thereof;

provided the compound is not N-((1S,5R,6R,E)-5,6-dihydroxy-4-(hydroxymethyl)-2-(((phenylcarbamoyl)oxy)imino)cyclohex-3-en-1-yl)acetamide having the formula:

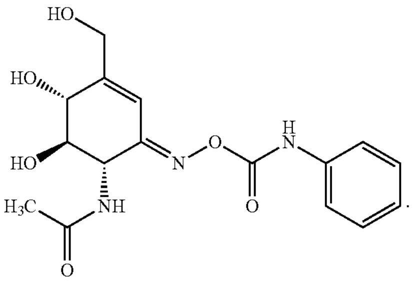 [SMILES: CC(=O)N[C@H]1/C(=N/OC(=O)Nc2ccccc2)C=C(CO)[C@@H](O)[C@@H]1O ; "."]

3. The compound of claim 1, wherein $R^1$ is $CO_2C_{1-3}$alkyl.

4. The compound of claim 1, wherein $R^2$ and $R^3$ are linked to form, together with the atoms to which they are attached, a 5-membered ring that is substituted with one or two methyl or ethyl groups.

5. The compound of claim 1, wherein one of $R^{4a}$ and $R^{4b}$ is $C_{1-4}$-acyl and the other is H.

6. The compound of claim 1, one of $R^{4a}$ and $R^{4b}$ is H or t-butoxycarbonyl, and the other is H.

7. The compound of claim 2, wherein $R^7$ is selected from R, OR, OH, NH(alkyl), N(alkyl)(alkyl), $NH_2$ and $Si(R)_3$, wherein each R is, independently, lower alkyl or aryl.

8. A compound of the formula III

III

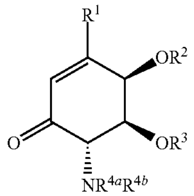

wherein $R^1$, $R^2$, $R^3$, $R^{4a}$ and $R^{4b}$ are as defined in claim 1.

9. The compound of claim 8 that is (3aR,7S,7aS)-ethyl-7-acetamido-2,2-dimethyl-6-oxo-3a,6,7,7a-tetrahydrobenzo[d][1,3]dioxole-4-carboxylate (compound 7), or a solvate thereof.

10. A compound of the formula IV:

IV

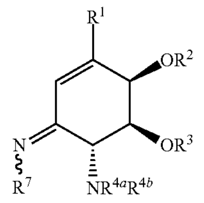

wherein $R^1$, $R^2$, $R^3$, $R^{4a}$, $R^{4b}$ and $R^7$ are as defined in claim 2.

11. The compound of claim 10 that is (3aR,7R,7aS)-ethyl-7-acetamido-6-(hydroxyimino)-2,2-dimethyl-3a,7,7a-tetrahydrobenzo[d][1,3]dioxole-4-carboxylate (compound 8), or a solvate thereof.

12. A compound of formula V:

V

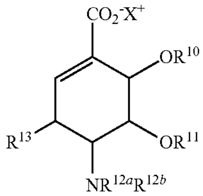

wherein $R^{10}$ and $R^{11}$ are independently selected from H, $C_{1-6}$alkyl and $C_{1-6}$acyl, or $R^{10}$ and $R^{11}$ are joined, together with the atoms to which they are attached, to form a 5-10-membered ring that is unsubstituted or substituted with one or more of halo or $C_{1-6}$alkyl;

$R^{12a}$ and $R^{12b}$ are independently selected from H, $C_{1-6}$alkyl and $C_{1-6}$acyl;

$R^{13}$ is selected from $OR^{14}$ and $NR^{15a}R^{15b}$ or $R^{13}$ is =O or =$NR^{16}$;

$R^{14}$ is selected from H, $C_{1-6}$alkyl and $C_{1-6}$acyl;

$R^{15a}$ and $R^{15b}$ are independently selected from H, $C_{1-6}$alkyl and $C_{1-6}$acyl;

$R^{16}$ is selected from H, OH, $C_{1-6}$alkyl, $OC_{1-6}$alkyl, $C_{1-6}$acyl, $OC_{1-6}$acyl, $NH_2$, $NHC_{1-6}$alkyl, $N(C_{1-6}$alkyl)($C_{1-6}$alkyl) and $NHC_{1-6}$acyl, or $R^{16}$ and one of $R^{12a}$ and $R^{12b}$ form a linker group "-A-C(O)—" to provide a compound of the formula:

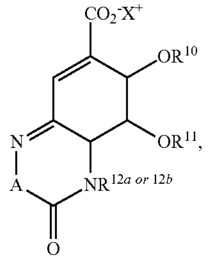

wherein A is O or NH;

$X^+$ is a cation;

and one or more available hydrogens in $R^{10}$, $R^{11}$, $R^{12a}$, $R^{12b}$, $R^{13}$, $R^{14}$, $R^{15a}$, $R^{15b}$ and/or $R^{16}$ is/are optionally replaced with F and/or one or more of available atoms in the compounds of the formula is/are optionally replaced with an isotopic label, or a pharmaceutically acceptable salt, and/or solvate thereof.

13. The compound of claim 12, wherein $R^{10}$ and $R^{11}$ are independently selected from H, $C_{1-4}$alkyl and $C_{1-4}$acyl, or $R^{10}$ and $R^{11}$ are joined, together with the atoms to which they are attached, to form a 5-6-membered ring that is unsubstituted or substituted with one or more of halo or $C_{1-4}$alkyl.

14. The compound of claim 13, wherein $R^{10}$ and $R^{11}$ are joined, together with the atoms to which they are attached, to form a 5-membered ring that is unsubstituted or substituted with one or two Me.

15. The compound of claim 12, wherein $R^{12a}$ and $R^{12b}$ are independently selected from H, $C_{1-4}$alkyl and $C_{1-4}$acyl.

16. The compound of claim 15, wherein one of $R^{12a}$ and $R^{12b}$ is H and the other is selected from Me, Et, C(O)Me and C(O)Et.

17. The compound of claim 12, wherein $R^{13}$ is selected from $OR^{14}$ or $R^{13}$ is =$NR^{16}$, where $R^{14}$ is selected from H, $C_{1-4}$alkyl and $C_{1-4}$acyl and $R^{16}$ is selected from H, OH, $C_{1-4}$alkyl, $OC_{1-4}$alkyl, $C_{1-4}$acyl, $OC_{1-4}$acyl $NH_2$, $NHC_{1-4}$ alkyl, $N(C_{1-4}$alkyl)($C_{1-4}$alkyl) and $NHC_{1-4}$acyl.

18. The compound of claim 17, wherein $R^{13}$ is selected from $OR^{14}$ or $R^{13}$ is =$NR^{16}$, where $R^{14}$ is selected from H, Me, Et, C(O)Me and C(O)Et and $R^{16}$ is selected from H, OH, Me, Et, OMe, OEt, C(O)Me, C(O)Et, OC(O)Me, OC(O)Et, $NH_2$, NHMe, NHEt, $N(Me)_2$, $N(Et)_2$, NHC(O)Me and NH(C(O)Et.

19. The compound of claim 12, wherein $R^{16}$ and one of $R^{12a}$ and $R^{12b}$ form a linker group "-A-C(O)—" to provide a compound of the formula:

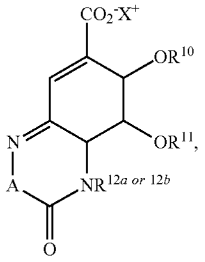

wherein A is O.

20. The compound of claim 19, wherein $R^{12}$ is $C_{1-6}$acyl.

21. The compound of claim 12, wherein $X^+$ is an alkali metal cation.

22. A compound of the formula V:

V

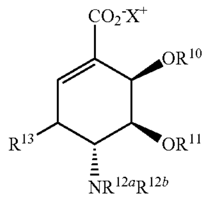

wherein $R^{10}$, $R^{11}$, $R^{12a}$, $R^{12b}$, $R^{13}$ and $X^+$ are as defined in claim 12, and one or more available hydrogens in $R^{10}$, $R^{11}$, $R^{12a}$, $R^{12b}$, $R^{13}$, $R^{14}$, $R^{15a}$, $R^{15b}$ and/or $R^{16}$ is/are optionally replaced with F and/or one or more of available atoms in the compounds of the formula is/are optionally replaced with an isotopic label, or a pharmaceutically acceptable salt, and/or solvate thereof.

23. The compound of claim 12, wherein the compound of formula V is: sodium (3aR,6R,7R,7aS)-7-acetamido-6-hydroxy-2,2-dimethyl-3a,6,7,7a-tetrahydrobenzo[d][1,3]dioxole-4-carboxylate (compound 19) or an alternate pharmaceutically acceptable salt thereof and/or a solvate thereof.

24. The compound of claim 22, that is sodium (3aR,7R,7aS,E)-7-acetamido-6-(hydroxyimino)-2,2-dimethyl-3a,6,7,7a-tetrahydrobenzo[d][1,3]dioxole-4-carboxylate (compound 17), or an alternate pharmaceutically acceptable salt thereof and/or a solvate and/or prodrug thereof.

25. The compound of claim 24, wherein the prodrug of the compound of formula V is the corresponding acid, $C_{1-20}$alkyl ester, $C_{6-14}$aryl ester or $C_{1-6}$alkylene$C_{6-14}$aryl ester.

26. A method of treating or preventing influenza comprising administering an effective amount of one or more compounds of the formula V:

V

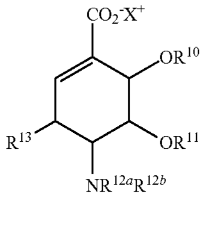

wherein $R^{10}$ and $R^{11}$ are independently selected from H, $C_{1-6}$alkyl and $C_{1-6}$acyl, or $R^{10}$ and $R^{11}$ are joined, together with the atoms to which they are attached, to form a 5-10-membered ring that is unsubstituted or substituted with one or more of halo or $C_{1-6}$alkyl;

$R^{12a}$ and $R^{12b}$ are independently selected from H, $C_{1-6}$alkyl and $C_{1-6}$acyl;

$R^{13}$ is selected from $OR^{14}$ and $NR^{15a}R^{15b}$ or $R^{13}$ is =O or $=NR^{16}$;

$R^{14}$ is selected from H, $C_{1-6}$alkyl and $C_{1-6}$acyl;

$R^{15a}$ and $R^{15b}$ are independently selected from H, $C_{1-6}$alkyl and $C_{1-6}$acyl;

$R^{16}$ is selected from H, OH, $C_{1-6}$alkyl, $OC_{1-6}$alkyl, $C_{1-6}$acyl, $OC_{1-6}$acyl, $NH_2$, $NHC_{1-6}$alkyl, $N(C_{1-6}$alkyl)($C_{1-6}$alkyl) and $NHC_{1-6}$acyl, or $R^{16}$ and one of $R^{12a}$ and $R^{12b}$ form a linker group "-A-C(O)—" to provide a compound of the formula:

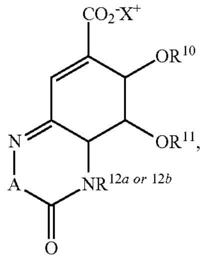

wherein A is O or NH;

$X^+$ is a cation;

and one or more available hydrogens in $R^{10}$, $R^{11}$, $R^{12a}$, $R^{12b}$, $R^{13}$, $R^{14}$, $R^{15a}$, $R^{15b}$ and/or $R^{16}$ is/are optionally replaced with F and/or one or more of available atoms in the compounds of the formula is/are optionally replaced with an isotopic label, or a pharmaceutically acceptable salt, and/or solvate thereof, to a subject in need thereof.

27. A pharmaceutical composition comprising one or more compounds of the formula V:

V

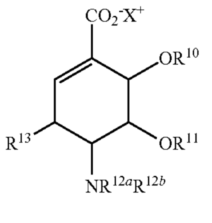

wherein $R^{10}$ and $R^{11}$ are independently selected from H, $C_{1-6}$alkyl and $C_{1-6}$acyl, or $R^{10}$ and $R^{11}$ are joined, together with the atoms to which they are attached, to form a 5-10-membered ring that is unsubstituted or substituted with one or more of halo or $C_{1-6}$alkyl;

$R^{12a}$ and $R^{12b}$ are independently selected from H, $C_{1-6}$alkyl and $C_{1-6}$acyl;

$R^{13}$ is selected from $OR^{14}$ and $NR^{15a}R^{15b}$ or $R^{13}$ is =O or $=NR^{16}$;

$R^{14}$ is selected from H, $C_{1-6}$alkyl and $C_{1-6}$acyl;

$R^{15a}$ and $R^{15b}$ are independently selected from H, $C_{1-6}$alkyl and $C_{1-6}$acyl;

$R^{16}$ is selected from H, OH, $C_{1-6}$alkyl, $OC_{1-6}$alkyl, $C_{1-6}$acyl, $OC_{1-6}$acyl, $NH_2$, $NHC_{1-6}$alkyl, $N(C_{1-6}$alkyl)($C_{1-6}$alkyl) and $NHC_{1-6}$acyl, or $R^{16}$ and one of $R^{12a}$ and $R^{12b}$ form a linker group "-A-C(O)—" to provide a compound of the formula:

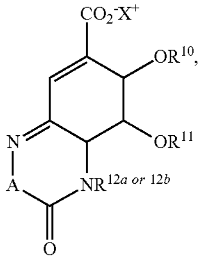

wherein A is O or NH;

$X^+$ is a cation;

and one or more available hydrogens in $R^{10}$, $R^{11}$, $R^{12a}$, $R^{12b}$, $R^{13}$, $R^{14}$, $R^{15a}$, $R^{15b}$ and/or $R^{16}$ is/are optionally replaced with F and/or one or more of available atoms in the compounds of the formula is/are optionally replaced with an isotopic label, or a pharmaceutically acceptable salt, and/or solvate thereof, and a pharmaceutically acceptable carrier and/or diluent.

28. The compound of claim 2, wherein $R^1$ is $CO_2C_{1-3}$alkyl.

29. The compound of claim 2, wherein $R^2$ and $R^3$ are linked to form, together with the atoms to which they are attached, a 5-membered ring that is substituted with one or two methyl or ethyl groups.

30. The compound of claim 2, wherein one of $R^{4a}$ and $R^{4b}$ is $C_{1-4}$acyl and the other is H.

31. The compound of claim 2, one of $R^{4a}$ and $R^{4b}$ is H or t-butoxycarbonyl, and the other is H.

32. The compound of claim 1, wherein $R^1$ is $C(O)O^-$, $CO_2Me$, $CO_2Et$, $CO_2iPr$, $CO_2nPr$, or $CO_2CH_2C{\equiv}CH$.

33. The compound of claim 2, wherein $R^1$ is $C(O)O^-$, $CO_2Me$, $CO_2Et$, $CO_2iPr$, $CO_2nPr$, or $CO_2CH_2C{\equiv}CH$.

34. The compound of claim 8, wherein $R^1$ is $C(O)O^-$, $CO_2Me$, $CO_2Et$, $CO_2iPr$, $CO_2nPr$, or $CO_2CH_2C{\equiv}CH$.

35. The compound of claim 23, wherein $R^1$ is $C(O)O^-$, $CO_2Me$, $CO_2Et$, $CO_2iPr$, $CO_2nPr$, or $CO_2CH_2C{\equiv}CH$.

* * * * *